US012207803B2

(12) United States Patent
Aljuri et al.

(10) Patent No.: US 12,207,803 B2
(45) Date of Patent: Jan. 28, 2025

(54) METHOD FOR REMOVING INTACT CELLS FROM A SURGICAL SITE

(71) Applicant: PROCEPT BioRobotics Corporation, Redwood City, CA (US)

(72) Inventors: Nikolai Aljuri, Hillsborough, CA (US); Surag Mantri, East Palo Alto, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 373 days.

(21) Appl. No.: 17/455,388

(22) Filed: Nov. 17, 2021

(65) Prior Publication Data

US 2022/0071606 A1   Mar. 10, 2022

Related U.S. Application Data

(60) Continuation of application No. 16/211,182, filed on Dec. 5, 2018, now Pat. No. 11,207,058, which is a
(Continued)

(51) Int. Cl.
*A61B 10/02* (2006.01)
*A61B 17/3203* (2006.01)
(Continued)

(52) U.S. Cl.
CPC .......... *A61B 10/02* (2013.01); *A61B 10/0241* (2013.01); *A61B 10/0275* (2013.01);
(Continued)

(58) Field of Classification Search
CPC ................ A61B 10/02; A61B 17/3203; A61B 17/32037; A61B 2017/32032;
(Continued)

(56) References Cited

U.S. PATENT DOCUMENTS

| 4,389,071 A | 6/1983 | Johnson, Jr. |
| 4,474,251 A | 10/1984 | Johnson, Jr. |

(Continued)

FOREIGN PATENT DOCUMENTS

| CN | 101394877 | 3/2009 |
| CN | 101460101 A | 6/2009 |

(Continued)

OTHER PUBLICATIONS

International Search Report and Written Opinion for International Application No. PCT/US2015/048687, 15 pages (Jan. 20, 2016).
(Continued)

*Primary Examiner* — Rene T Towa
*Assistant Examiner* — Huong Q. Nguyen
(74) *Attorney, Agent, or Firm* — FisherBroyles, LLP; John K. Shimmick

(57) ABSTRACT

A surgical treatment apparatus comprises a waterjet configured to fragment tissue and provide intact cells such as stem cells with the fragmented tissue. The intact cells can be used in one or more of many ways such as for genetic or other testing. In many embodiments, the intact cells comprise stem cells. In many embodiments, a waterjet is configured to fragment tissue. The fragmented tissue can be collected with a filter having pores sized smaller than the tissue fragments. In many embodiments cavitation with a waterjet is used to fragment the tissue comprising the intact stem cells. The waterjet may comprise a waterjet immersed in a liquid comprising water so as to form a plurality of shedding pulses. The plurality of shedding pulses can be generated with a frequency sufficient to fragment the tissue. The shedding pulses can generate cavitations that fragment the tissue.

19 Claims, 21 Drawing Sheets

Related U.S. Application Data division of application No. 15/446,749, filed on Mar. 1, 2017, now Pat. No. 10,588,609, which is a continuation of application No. PCT/US2015/048687, filed on Sep. 4, 2015.

(60) Provisional application No. 62/046,290, filed on Sep. 5, 2014.

(51) Int. Cl.
 G01N 1/00 (2006.01)
 A61B 17/00 (2006.01)
 A61B 34/30 (2016.01)

(52) U.S. Cl.
 CPC ............ *A61B 10/0283* (2013.01); *G01N 1/00* (2013.01); *A61B 2017/00274* (2013.01); *A61B 2017/32032* (2013.01); *A61B 34/30* (2016.02); *A61B 2217/005* (2013.01); *A61B 2217/007* (2013.01)

(58) Field of Classification Search
 CPC ...... A61B 2017/32035; A61B 10/0241; A61B 2017/00274; A61M 3/0275
 See application file for complete search history.

(56) References Cited

U.S. PATENT DOCUMENTS

| | | | |
|---|---|---|---|
| 4,672,963 A | 6/1987 | Barken | |
| 5,135,482 A | 8/1992 | Neracher | |
| 5,269,785 A | 12/1993 | Bonutti | |
| 5,322,504 A | 6/1994 | Doherty | |
| 5,558,634 A | 9/1996 | Mitchell | |
| 5,833,701 A | 11/1998 | Gordon | |
| 5,871,462 A | 2/1999 | Yoder | |
| 6,071,284 A | 6/2000 | Fox | |
| 6,217,543 B1 | 4/2001 | Anis | |
| 6,228,046 B1 | 5/2001 | Brisken | |
| 6,375,635 B1 | 4/2002 | Moutafis | |
| 6,440,105 B1 | 8/2002 | Menne | |
| 6,572,578 B1 | 6/2003 | Blanchard | |
| 7,008,421 B2 | 3/2006 | Daniel | |
| 7,115,100 B2 | 10/2006 | Mcrury | |
| 7,882,841 B2 | 2/2011 | Aljuri | |
| 8,092,507 B2 | 1/2012 | Tomasello | |
| 8,419,723 B2 | 4/2013 | Shadduck | |
| 8,795,194 B2 | 8/2014 | Howard | |
| 8,814,921 B2 | 8/2014 | Aljuri | |
| 9,232,959 B2 | 1/2016 | Aljuri | |
| 9,232,960 B2 | 1/2016 | Aljuri | |
| 9,237,902 B2 | 1/2016 | Aljuri | |
| 9,364,250 B2 | 6/2016 | Aljuri | |
| 9,364,251 B2 | 6/2016 | Aljuri | |
| 9,510,853 B2 | 12/2016 | Aljuri | |
| 9,668,764 B2 | 6/2017 | Aljuri | |
| 9,848,904 B2 | 12/2017 | Aljuri | |
| 9,867,635 B2 | 1/2018 | Alvarez | |
| 9,931,445 B2 | 4/2018 | Pustilnik | |
| 10,448,966 B2 | 10/2019 | Aljuri | |
| 2001/0002562 A1 | 6/2001 | Moutafis | |
| 2002/0022869 A1 | 2/2002 | Hareyama | |
| 2002/0045911 A1 | 4/2002 | Fletcher | |
| 2003/0036768 A1 | 2/2003 | Hutchins | |
| 2003/0139041 A1 | 7/2003 | Leclair | |
| 2003/0161816 A1* | 8/2003 | Fraser ..................... A61P 27/02 424/93.7 |
| 2004/0097829 A1 | 5/2004 | Mcrury | |
| 2004/0230211 A1 | 11/2004 | Moutafis | |
| 2005/0004516 A1 | 1/2005 | Vanney | |
| 2006/0030787 A1 | 2/2006 | Quay | |
| 2006/0089626 A1 | 4/2006 | Vlegele | |
| 2006/0118495 A1 | 6/2006 | Kondratalv | |
| 2007/0230757 A1 | 10/2007 | Trachtenberg | |
| 2007/0270714 A1 | 11/2007 | Cushner | |
| 2008/0178654 A1 | 7/2008 | Hochmitz | |
| 2008/0253527 A1 | 10/2008 | Boyden | |
| 2009/0088775 A1 | 4/2009 | Swarup | |
| 2010/0010524 A1 | 1/2010 | Barrington | |
| 2010/0076269 A1 | 3/2010 | Makower | |
| 2010/0145326 A1 | 6/2010 | Hoey | |
| 2010/0179522 A1 | 7/2010 | Companion | |
| 2010/0179528 A1 | 7/2010 | Shadduck | |
| 2011/0104800 A1 | 5/2011 | Kensy | |
| 2011/0184291 A1 | 7/2011 | Okamura | |
| 2011/0184391 A1 | 7/2011 | Aljuri | |
| 2012/0065656 A1 | 3/2012 | Karwei | |
| 2012/0157841 A1 | 6/2012 | Glaenzer | |
| 2013/0158534 A1 | 6/2013 | Hoey | |
| 2013/0261540 A1 | 10/2013 | Crank | |
| 2014/0058361 A1 | 2/2014 | Gordon | |
| 2014/0193833 A1 | 7/2014 | Srivastava | |
| 2014/0249547 A1 | 9/2014 | Boone, III | |
| 2014/0309649 A1 | 10/2014 | Alvarez | |
| 2015/0025539 A1 | 1/2015 | Alvarez | |
| 2015/0045777 A1 | 2/2015 | Aljuri | |
| 2015/0057646 A1 | 2/2015 | Aljuri | |
| 2015/0088107 A1 | 3/2015 | Aljuri | |
| 2015/0088110 A1 | 3/2015 | Aljuri | |
| 2015/0313666 A1 | 11/2015 | Aljuri | |
| 2015/0335344 A1 | 11/2015 | Aljuri | |
| 2016/0074059 A1 | 3/2016 | Aljuri | |
| 2016/0143778 A1 | 5/2016 | Aljuri | |
| 2016/0228141 A1 | 8/2016 | Aljuri | |
| 2017/0172548 A1 | 6/2017 | Aljuri | |
| 2017/0172668 A1 | 6/2017 | Aljuri | |
| 2017/0231655 A1 | 8/2017 | Aljuri | |
| 2018/0263647 A1 | 9/2018 | Aljuri | |

FOREIGN PATENT DOCUMENTS

| | | |
|---|---|---|
| CN | 102271595 A | 12/2011 |
| CN | 102271602 | 12/2011 |
| CN | 102905633 | 1/2013 |
| CN | 103118611 | 5/2013 |
| CN | 103764056 | 4/2014 |
| EP | 1075853 A2 | 2/2001 |
| EP | 3188667 A1 | 7/2017 |
| JP | 2001046528 A | 2/2001 |
| JP | 2003528684 A | 9/2003 |
| JP | 2004170414 A | 6/2004 |
| JP | 2007020837 A | 2/2007 |
| JP | 2007068636 A | 3/2007 |
| JP | 2010532178 A | 10/2010 |
| JP | 2012508068 A | 4/2012 |
| JP | 2012523253 A | 10/2012 |
| JP | 2013518684 A | 5/2013 |
| WO | 03088833 A1 | 10/2003 |
| WO | 2004004914 | 1/2004 |
| WO | 2004028592 A1 | 4/2004 |
| WO | 2004080529 A2 | 9/2004 |
| WO | 2006089426 A1 | 8/2006 |
| WO | 2007101015 A1 | 9/2007 |
| WO | 2008083407 A1 | 7/2008 |
| WO | 2009029461 A1 | 3/2009 |
| WO | 2009111736 A1 | 9/2009 |
| WO | 2009152613 A1 | 12/2009 |
| WO | 2010054220 A1 | 5/2010 |
| WO | 2010144419 A2 | 12/2010 |
| WO | 2011097505 A1 | 8/2011 |
| WO | 2011100753 A2 | 8/2011 |
| WO | 2011141775 A1 | 11/2011 |
| WO | 2013129657 A1 | 9/2013 |
| WO | 2013130895 A1 | 9/2013 |
| WO | 2014127242 | 8/2014 |
| WO | 2014165703 A1 | 10/2014 |
| WO | 2015035249 A2 | 3/2015 |
| WO | 2015200538 A1 | 12/2015 |
| WO | 2016004071 A1 | 1/2016 |

(56) References Cited

FOREIGN PATENT DOCUMENTS

| | | |
|---|---|---|
| WO | 2016037132 A1 | 3/2016 |
| WO | 2016037137 A1 | 3/2016 |

OTHER PUBLICATIONS

Nishimura, et al. Similarity Law on Shedding Frequency of Cavitation Cloud Induced by a Cavitating Jet. Journal of Fluid Science and Technology, vol. 7, No. 3, 2012, pp. 405-420.

Prajapati, et al., Pluripotent Stem Cell within the Prostate could be Responsible for Benign Prostate Hyperplasia in Human, J Stem Cell Res Ther2014, 4:1.

Prajapati, et al., Prostate Stem Cells in the Development of Benign Prostate Hyperplasia and Prostate Cancer: Emerging Role and Concepts, Biomed Res Int 2013; 2013:107954.

Ruggeri, et al., Activation-independent platelet adhesion and aggregation under elevated shear stress. Blood. Sep. 15, 2006; 108(6):1903-1910.

Adachi, Yasunori, et al., "Cavitation Noise Characteristics around High-Speed Submerged Water Jets," Transactions of the Japan Society of Mechanical Engineers, Part B, 60(571):730-735 (1994).

Hutli, Ezddin A.F., et al., "Frequency in Shedding/Discharging Cavitation Clouds Determined by Visualization of a Submerged Cavitating Jet," Journal of Fluids Engineering, vol. 130, pp. 38-45 (Feb. 2008).

J. Gaythwaite, The Marine Environment and Structural Design, book, 1992.4, pp. 30-33, China Ocean Press, China, with English machine translation.

Jun Li and Fuhai Li, Detechtion Technolody and Instrument, book, 2000.6, pp. 233-235, China Light Industry Press, China, with English machine translation.

Soyama, Hitoshi, et al., "Enhancement of Impact Force around a Cavitating Jet by Changing with Nozzle Outlet Geometry," Japan Society of Mechanical Engineers, pp. 77-85 (2009).

Tang, Chuanlin, et al., "Effects of Upstream Oscillating Flow on the Self-Excited Oscillation Pulsed Jet," 994-2023 China Academic Journal Electronic Publishing House; http://www.cnki.net, pp. 24-27 (2001). English abstract at end of article.

Xunyi Wu, Automatic Detection Technology—Previous Volume, book, 1981.1, pp. 115-118, China Machine Press, China, with English machine translation.

Yamauchi, Yoshiaki, et al., "Formation Process of Vortex Ring Cavitation in High-Speed Submerged Water Jets," Transactions of the Japan Society of Mechanical Engineers, B, No. 95-0502, pp. 72-78 (1996), with English machine translation.

\* cited by examiner

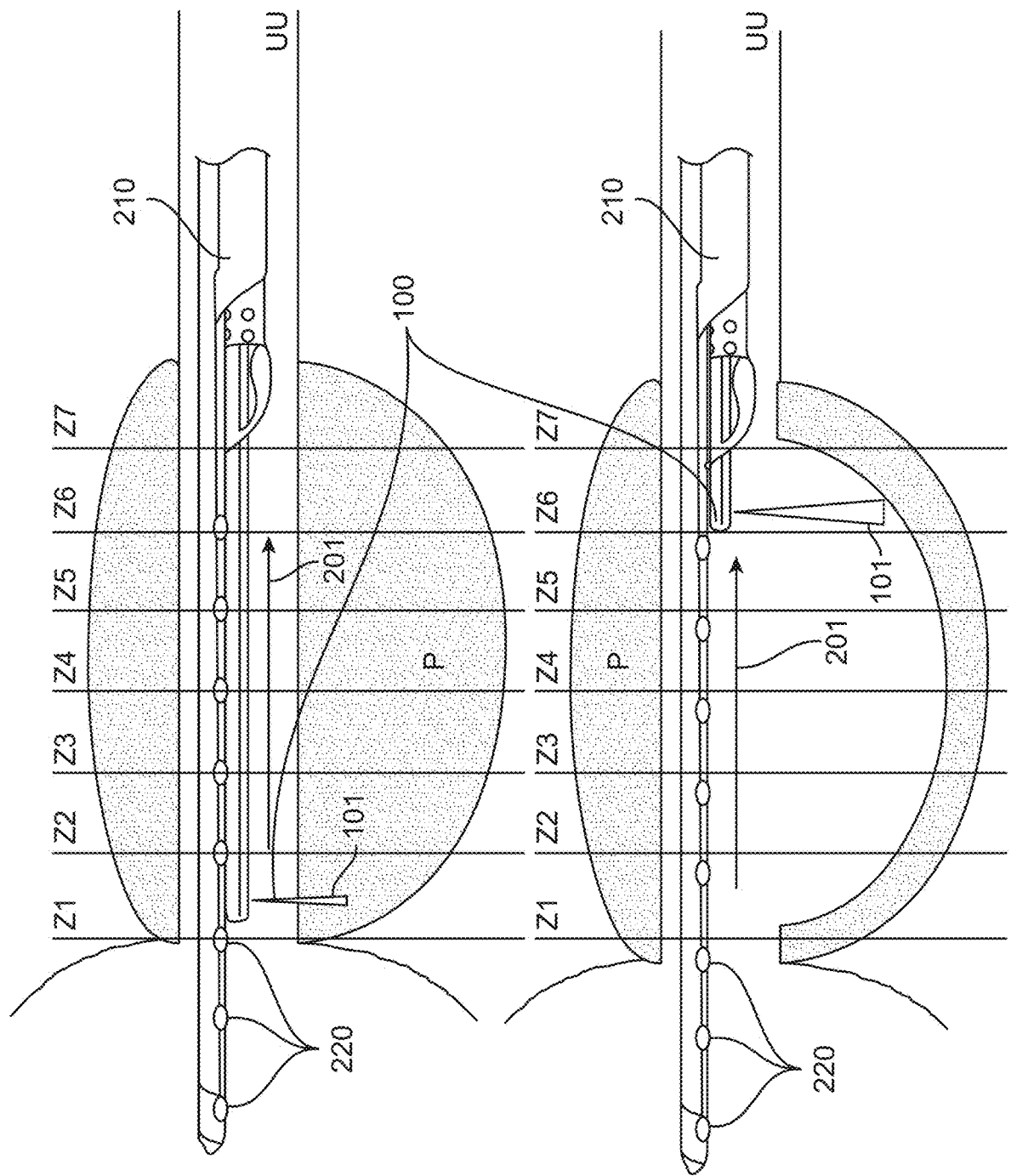

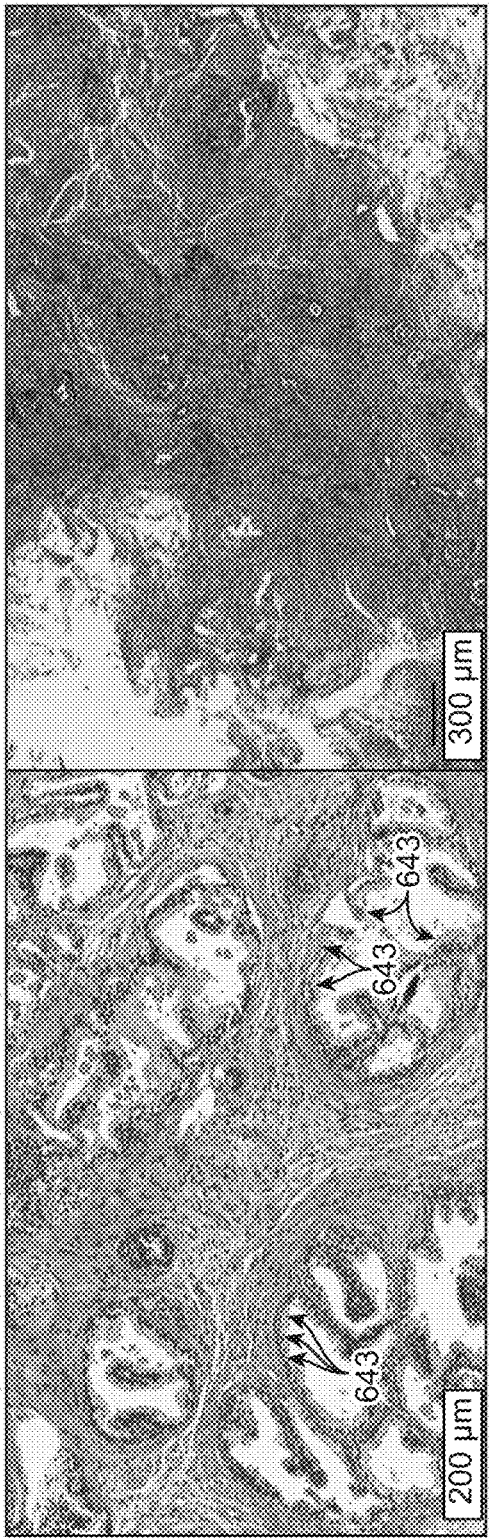
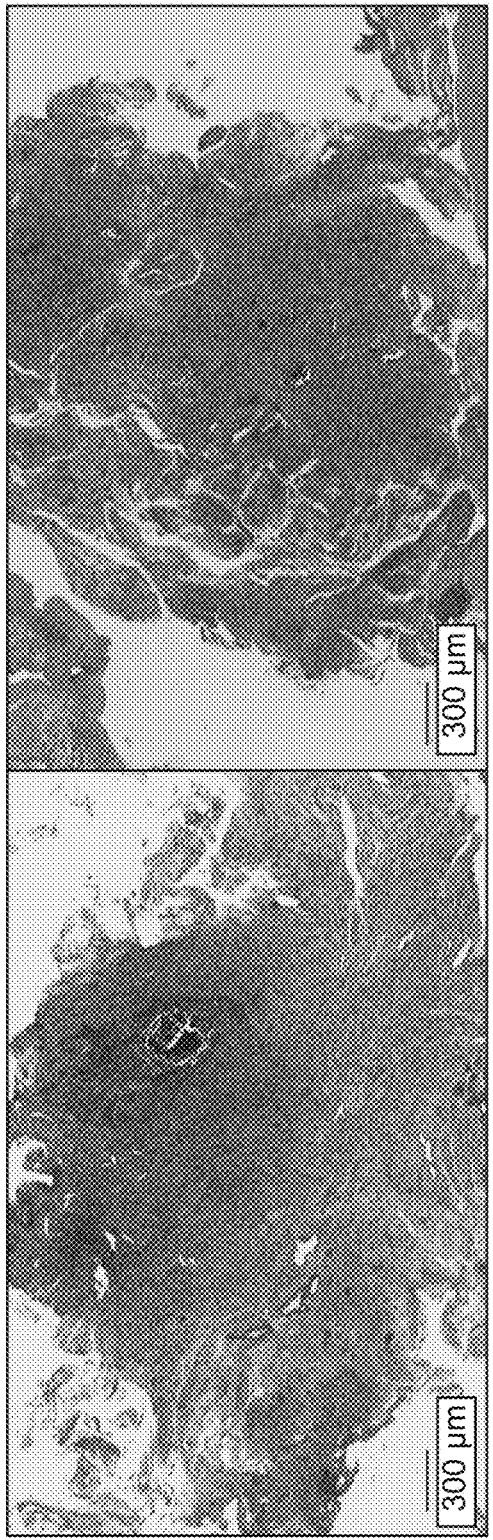
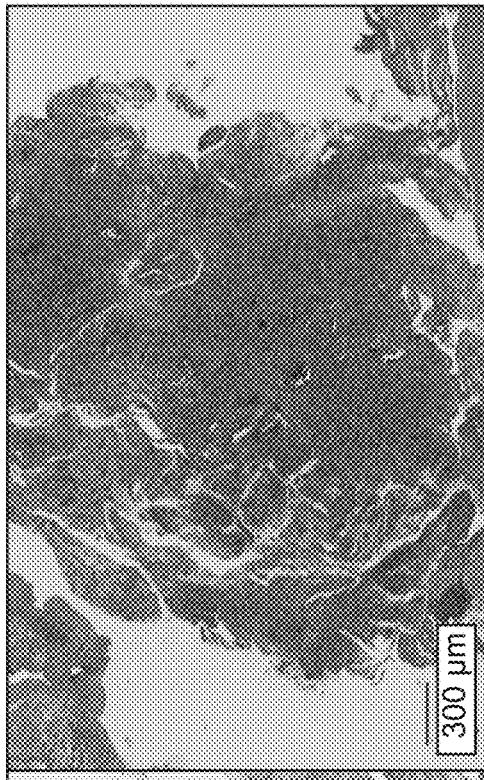
FIG. 10A  Subject 3 (slide C) – Higher Magnification
FIG. 10B  Subject 4 – Age 64
FIG. 10C  Subject 1 – Age 67
FIG. 10D  Subject 2 – Age 66

METHOD FOR REMOVING INTACT CELLS FROM A SURGICAL SITE

CROSS-REFERENCE

This application is a continuation of U.S. patent application Ser. No. 16/211,182, filed Dec. 5, 2018, now U.S. Pat. No. 11,207,058, issued Dec. 28, 2021, which is a division of U.S. patent application Ser. No. 15/446,749, filed Mar. 1, 2017, now U.S. Pat. No. 10,588,609, issued Mar. 17, 2020, which is a continuation of International Application Serial No. PCT/US2015/048687, filed Sep. 4, 2015, published as WO 2016/037132 on Mar. 10, 2016, entitled "GENE ANALYSIS AND GENERATION OF STEM CELL METHODS AND APPARATUS," which claims priority to U.S. Provisional Patent Application No. 62/046,290, filed Sep. 5, 2014, entitled "GENE ANALYSIS AND GENERATION OF STEM CELL METHODS AND APPARATUS," the entire disclosures of which are incorporated herein by reference.

The subject matter of the present application is related to: PCT/US2013/028441, filed Feb. 28, 2013, published as WO 2013/130895 on Sep. 6, 2013, entitled "AUTOMATED IMAGE-GUIDED TISSUE RESECTION AND TREATMENT;" U.S. Provisional Patent Application No. 61/874,849, filed Sep. 6, 2013, entitled "AUTOMATED IMAGE-GUIDED TISSUE RESECTION AND TREATMENT;" U.S. Provisional Patent Application No. 61/972,730, filed Mar. 31, 2014, entitled "AUTOMATED IMAGE-GUIDED TISSUE RESECTION AND TREATMENT;" U.S. Provisional Patent Application No. 62/019,305, filed Jun. 30, 2014, entitled "AUTOMATED IMAGE-GUIDED TISSUE RESECTION AND TREATMENT;" U.S. Provisional Patent Application No. 62/018,359, filed Jun. 27, 2014, entitled "TISSUE SAMPLING AND TREATMENT METHODS AND APPARATUS;" U.S. Provisional Patent Application No. 62/019,299, filed Jun. 30, 2014, entitled "FLUID JET TISSUE ABLATION AND INDUCED HEMOSTATIS (AQUABLATION) METHODS AND APPARATUS;" the entire disclosures of which are incorporated herein by reference.

The subject matter of the present patent application is also related to: U.S. patent application Ser. No. 12/700,568, filed Feb. 4, 2010, entitled "MULTI FLUID TISSUE RESECTION METHODS AND DEVICES," now U.S. Pat. No. 9,232,959, issued Jan. 12, 2016; and International Application PCT/US2011/023781 filed Feb. 4, 2011, published as WO 2011/097505 on Nov. 8, 2011, entitled "MULTI FLUID TISSUE RESECTION METHODS AND DEVICES;" the full disclosures of which are incorporated herein by reference.

BACKGROUND

The field of the present invention is related to the sampling of cells and tissue and treatment of tissue, and more specifically to the sampling and treatment of an organ such as the prostate.

Prior methods and apparatus of treating subjects such as patients can result in less than ideal results in at least some instances. For example, prior methods of prostate surgery can result in longer healing time and less than ideal outcomes in at least some instances.

Although early diagnosis and treatment of cancer can provide improved outcomes, the prior methods and apparatus of diagnosing and treating cancer can be less than ideal. In at least some instances, patients having benign prostate hyperplasia (BPH) may also have prostate cancer (PCa), which may not be diagnosed as quickly as would be ideal. Also, the prior methods and apparatus for treating cancer may be less than ideally suited for combination with other treatments, for example.

Many organs such as the prostate comprise an outer wall or capsule, which comprises sensitive nerves or blood vessels. Damage to the nerves or vessels can lead to decreased functioning of the organ, and the prior methods and apparatus can provide less than ideal removal of tissue near capsules and walls of organs. For example, damage to nerves of the prostate capsule may lead to decreased potency, and damage to the optic nerve or vessels of the eye can lead to decreased vision in at least some instances.

Also, the prior methods and apparatus for sampling of tissue to collect cells may result in less ideal results in at least some instances. It would be desirable to provide a means for removing intact cells from a patient, so that the cells may be used for diagnostic or other applications. For example, stem cells are known to play an important role in many cancers and may be suitable test targets for the diagnosis of the cancers. Prostate stem cells, for example, have been implicated in the development of prostate disease states, including BPH and prostate cancer. In addition, the cell lines generated from the sampled tissue may have valuable uses in cancer research and therapies such as cell-based therapies.

In light of the above, it would be helpful to provide improved methods and apparatus for surgery and diagnosing and treating cancer. Ideally such methods would provide improved treatment of delicate tissue structures such as nerves and vessels of the organ, and determine the presence or absence of cancer and provide improved treatments with improved outcomes.

SUMMARY

Embodiments of the present invention provide improved methods and apparatus for collecting tissue samples with intact cells. A surgical treatment apparatus comprises a waterjet configured to fragment tissue and provide intact cells such as stem cells with the fragmented tissue. The intact cells can be used in one or more of many ways such as for genetic or other testing, and the intact cells can be identified as stem cells. In many embodiments, the intact cells comprise stem cells. The harvested stem cells can be used in one or more of many ways, and can be used to generate lines of pluripotent stem cells, or to diagnose the patient. In many embodiments, a waterjet is configured to fragment tissue. The fragmented tissue can be collected with a filter having pores sized smaller than the tissue fragments. In many embodiments cavitation with a waterjet is used to fragment the tissue comprising the intact stem cells. The waterjet may comprise a waterjet immersed in a liquid comprising water so as to form a plurality of shedding pulses in order to fragment the tissue. The plurality of shedding pulses can be generated with a frequency sufficient to fragment the tissue. The shedding pulses can comprise vapor cavities that can coalesce into cavitation clouds that fragment the tissue.

In many embodiments, a substantially fixed flow rate system is used to harvest the fragmented tissue. A rate of fluid flow into a surgical site may match substantially a fluid flow out of the surgical site in order to inhibit changes to the volume of the surgical site. A pump can be configured to draw fluid comprising the fragments from the site at a rate similar to the flow of the waterjet. When insufflation is used, the rate of draw from the site can be similar to the combined flow of the jet and insufflation, although insufflation may not be provided in at least some embodiments. In many embodiments, a fluid reservoir is coupled to the surgical site with a slight pressure, in order to inhibit substantial changes in pressure with changes in volume of the surgical site.

While embodiments of the present invention are specifically directed at transurethral treatment of the prostate, certain aspects of the invention may also be used to treat and collect tissue of other organs such as brain, heart, lungs, intestines, eyes, skin, kidney, liver, pancreas, stomach, uterus, ovaries, testicles, bladder, car, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 9A-9D show the apparatus of FIG. 6 adapted to remove intact cells from localized zones of the surgical site, in accordance with embodiments;

FIGS. 10A to 10D show images of histological sections of prostate tissue removed from patients using the apparatus of as described herein.

DETAILED DESCRIPTION

Figure 1:
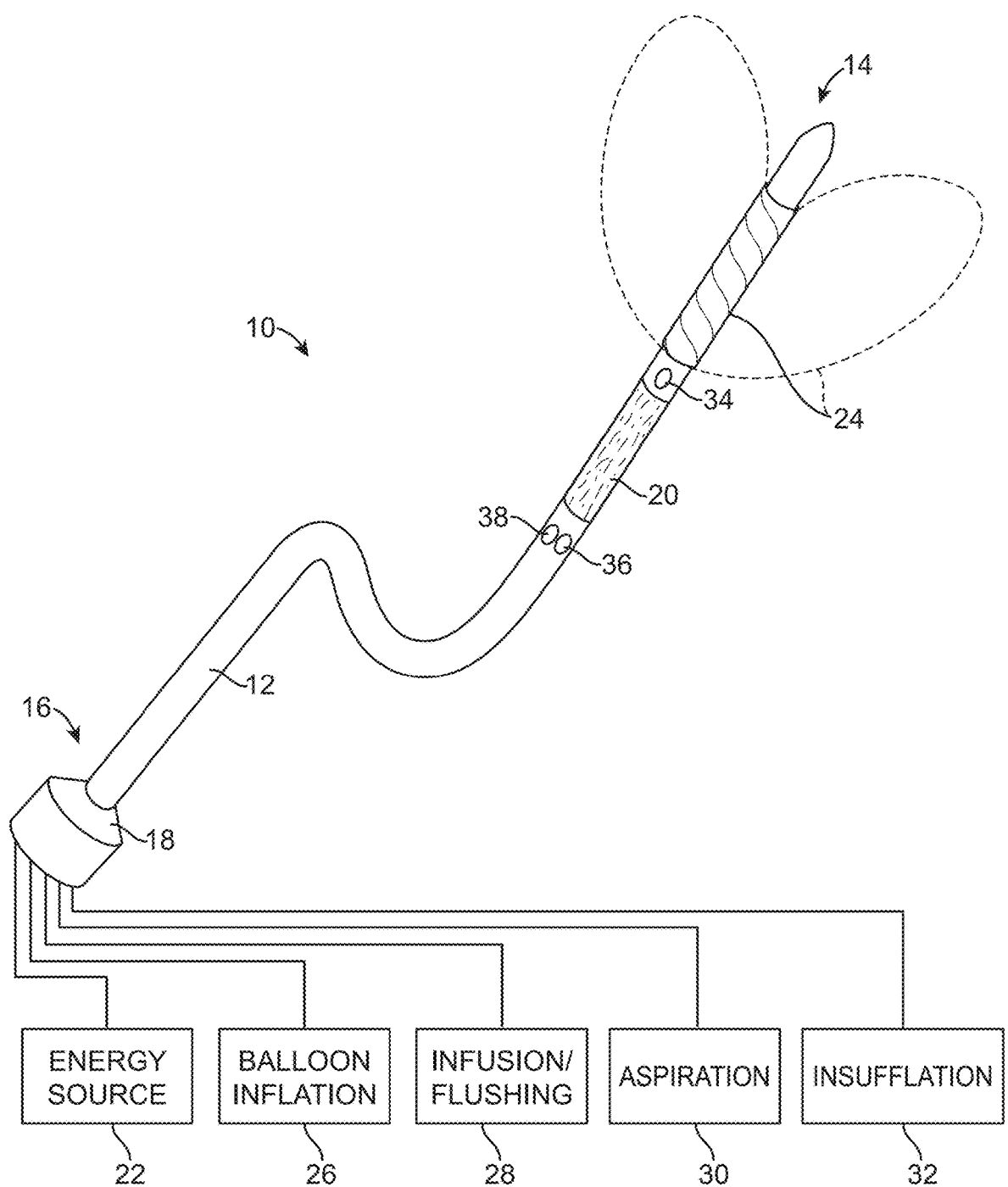
FIG. 1 is a schematic illustration of a device suitable for performing intraurethral prostatic tissue debulking in accordance with embodiments.

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described herein.

The embodiments as disclosed herein can be used to collect fat cells and prostate tissue, and many other types of tissue, such as tissue from other organs, for example. The embodiments as disclosed herein are well suited to collect cells related to cancer, and can be used to detect biomarkers on the surfaces of the intact harvested cells. Alternatively or in combination, genetic testing can be performed with the cells harvested. In many embodiments, the cells can be used to generate lines of pluripotent stem cells, for example.

The methods and apparatus as disclosed herein are well suited for use with many other tissues in addition to the prostate. With embodiments related to prostate tissue for example, the cell tissue harvesting methods and apparatus as disclosed herein allow the surgeon to treat the prostate and harvest tissue, for example.

The embodiments disclosed herein can be combined in one or more of many ways to provide improved therapy to a patient. The disclosed embodiments can be combined with prior methods and apparatus to provide improved treatment, such as combination with known methods of prostate surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments. Methods and apparatus of tissue removal suitable for incorporation in accordance with embodiments as disclosed herein are described in: PCT/US2013/028441, filed Feb. 28, 2013, entitled "AUTOMATED IMAGE-GUIDED TISSUE RESECTION AND TREATMENT;" U.S. Provisional Patent Application No. 61/874,849, filed Sep. 6, 2013, entitled "AUTOMATED IMAGE-GUIDED TISSUE RESECTION AND TREATMENT;" U.S. Provisional Patent Application No. 61/972,730, filed Mar. 31, 2014, entitled "AUTOMATED IMAGE-GUIDED TISSUE RESECTION AND TREATMENT;" U.S. Provisional Patent Application No. 62/019,305, filed Jun. 30, 2014, entitled "AUTOMATED IMAGE-GUIDED TISSUE RESECTION AND TREATMENT;" U.S. Provisional Patent Application No. 62/018, 359, filed Jun. 27, 2014, entitled "TISSUE SAMPLING AND TREATMENT METHODS AND APPARATUS;" U.S. Provisional Patent Application No. 62/019,299, filed Jun. 30, 2014, entitled "FLUID JET TISSUE ABLATION AND INDUCED HEMOSTATIS (AQUABLATION) METHODS AND APPARATUS;" the entire disclosures of which have been previously incorporated herein by reference.

Although the cell harvesting as described herein is presented in the context of prostate surgery, the methods and apparatus as described herein can be used to harvest cells from any tissue of the body and any organ and vessel of the body such as brain, heart, lungs, intestines, eyes, skin, kidney, liver, pancreas, stomach, uterus, ovaries, testicles, bladder, car, nose, mouth, soft tissues such as bone marrow, adipose tissue, muscle, glandular and mucosal tissue, spinal and nerve tissue, cartilage, hard biological tissues such as teeth, bone, etc., as well as body lumens and passages such as the sinuses, ureter, colon, esophagus, lung passages, blood vessels and throat.

As used herein, A and/or B encompasses A, or B, and combinations thereof.

As used herein, the term Aquablation encompasses ablation with water or any other fluid.

As used herein, the words scope, telescope, endoscope and cytoscope are used interchangeably.

As used herein, the terms AquaBeam, flame, fluid flame, fluid cloud, entrainment region, and cavitation region are used interchangeably.

As used herein a processor encompasses one or more processors, for example a single processor, or a plurality of processors of a distributed processing system for example. A controller or processor as described herein generally comprises a tangible medium to store instructions to implement a steps of a process, and the processor may comprise one or more of a central processing unit, programmable array logic, gate array logic, or a field programmable gate array, for example.

As used herein like characters and numerals identify like elements.

As used herein, a real time image shown on a display encompasses an image shown within a few seconds of the event shown. For example, real time imaging of a tissue structure encompasses providing the real time image on a display within about ten seconds of the image being acquired.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

Automated robotic control—where movement of the waterjet is motorized and under computer control with preselected routines-allows accurate and finely detailed resections not possible with manual control. Advantages include reduced time required for procedures, fewer complications, improved outcomes and less training time needed for surgeons. Many of these improvements arise from reducing or eliminating the need for manual dexterity of the treating physician. Automatic control further allows the cutting power of the nozzle to be increased to levels not achievable with full manual control. The system may be manually controlled during less critical portions of the procedure, e.g. during initial selection of an area to operate on and for touch-ups in cutting and cautery. Even during these less critical phases of the protocols, the increased precision and smoothness provided by the automated control can provide reduction and filtering of hand jitter. Another significant advantage is that automation allows for pretesting or "dry runs" of a procedure. When a cutting routine is selected, the limits of area can be selected using a joystick or other control element to position the laser during a mock the procedure without cutting. Changes can be made before cutting commences, so that errors can be corrected before beginning the actual procedure.

INCORPORATION BY REFERENCE

Figure 2A:
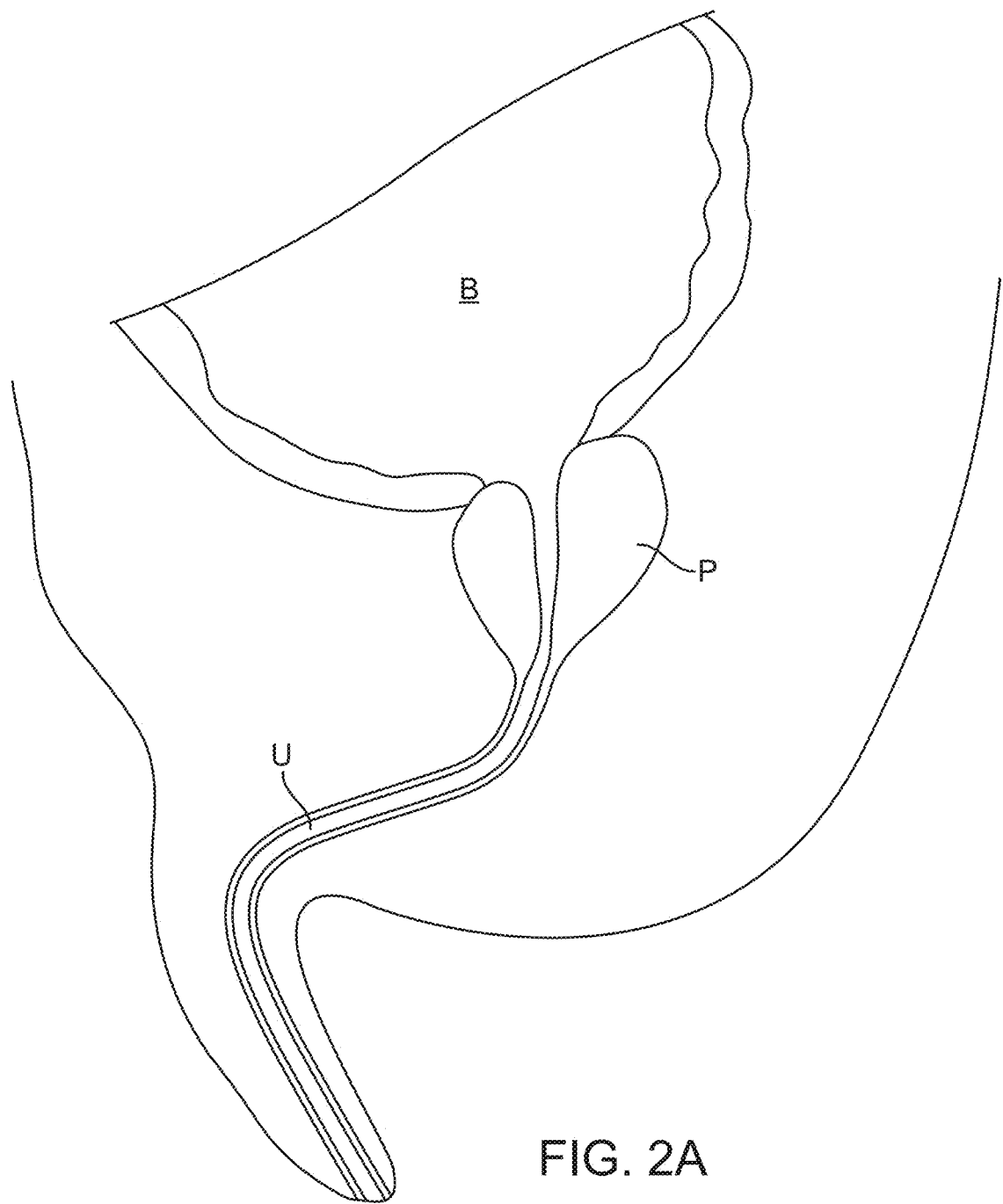
FIGS. 2A-2D illustrate use of the device of FIG. 1 in performing prostatic tissue debulking.
Figure 2B:
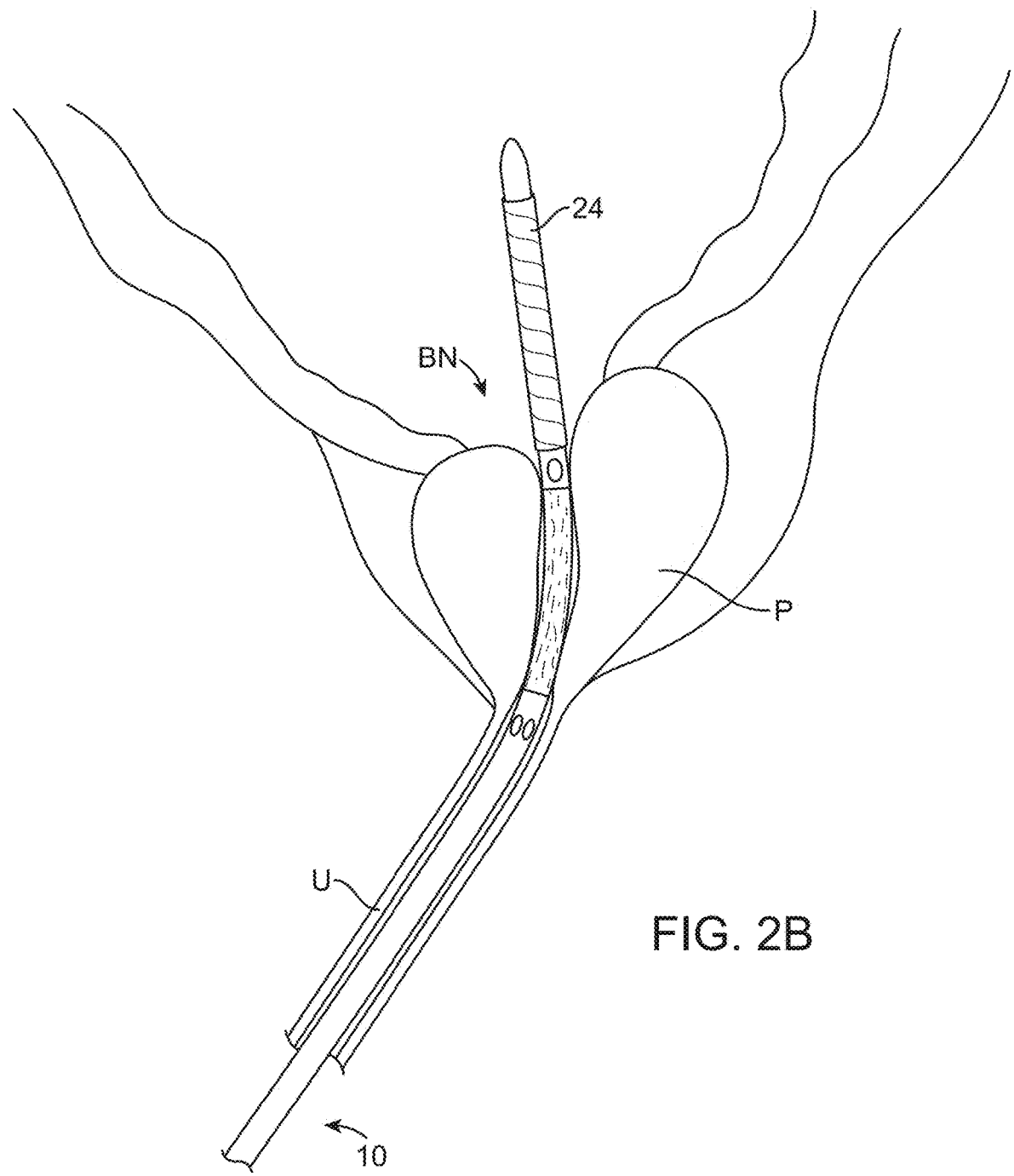
Figure 2C:
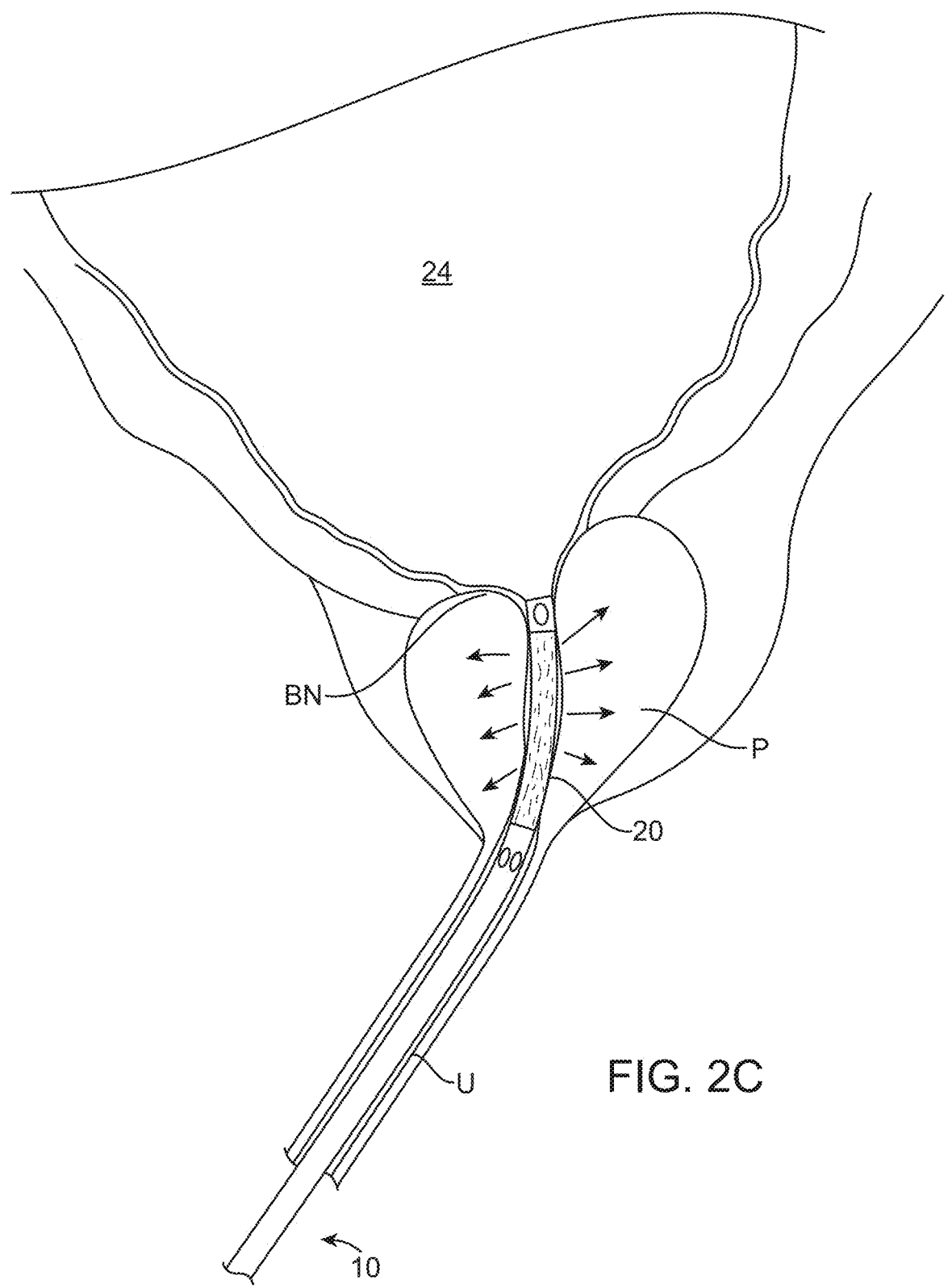
Figure 2D:
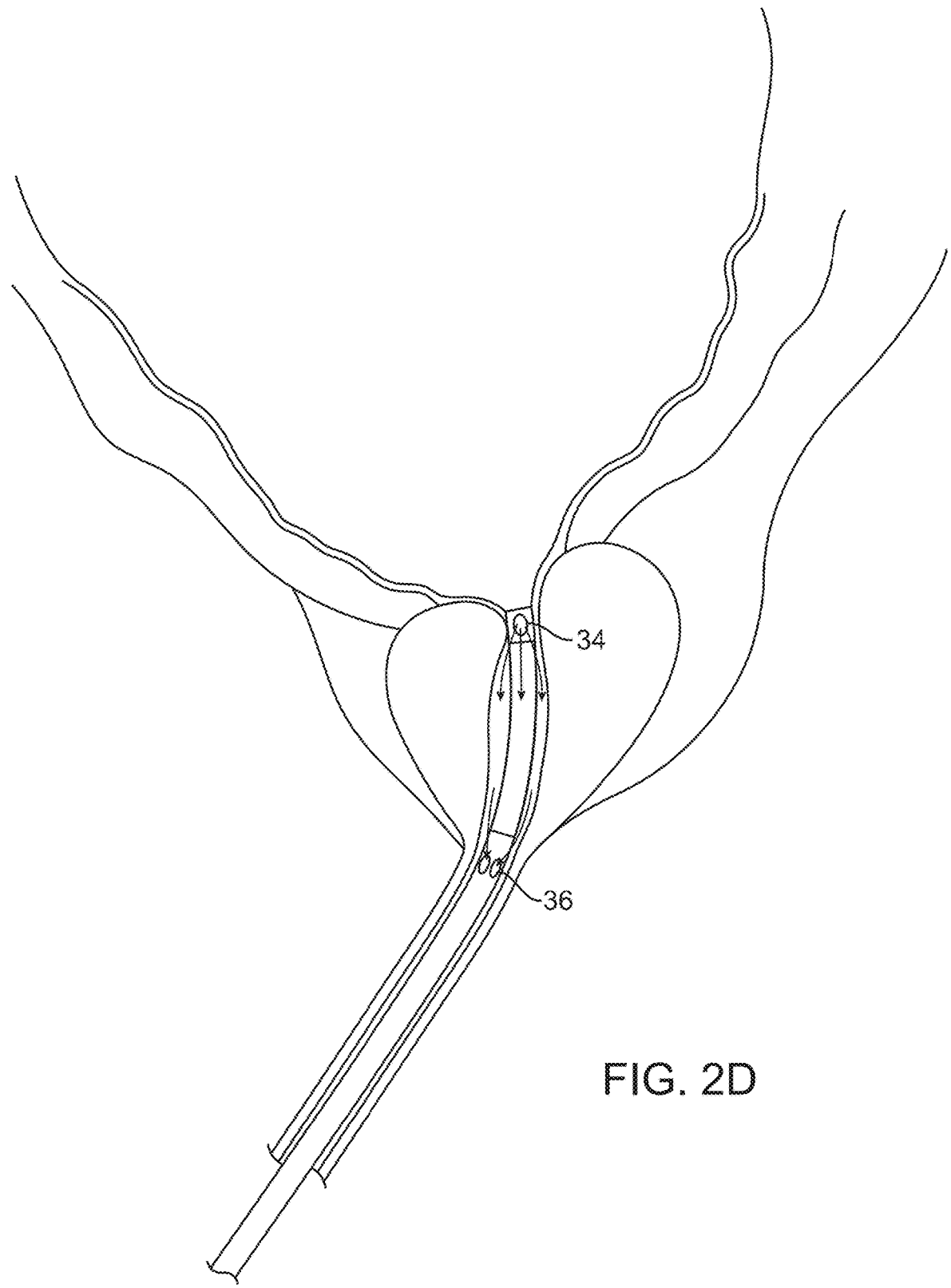

The subject matter of FIGS. 1 to 2D and the corresponding text have been incorporated by reference as described in: U.S. patent application Ser. No. 12/700,568, filed Feb. 4, 2010, entitled "MULTI FLUID TISSUE RESECTION METHODS AND DEVICES," now U.S. Pat. No. 9,232,959, issued Jan. 12, 2016; and International Application PCT/US2011/023781, filed Feb. 4, 2011, published as WO 2011/097505 on Nov. 8, 2011, entitled "MULTI FLUID TISSUE RESECTION METHODS AND DEVICES;" the full disclosures of which have been previously incorporated herein by reference.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized CO2 or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2C. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3A:
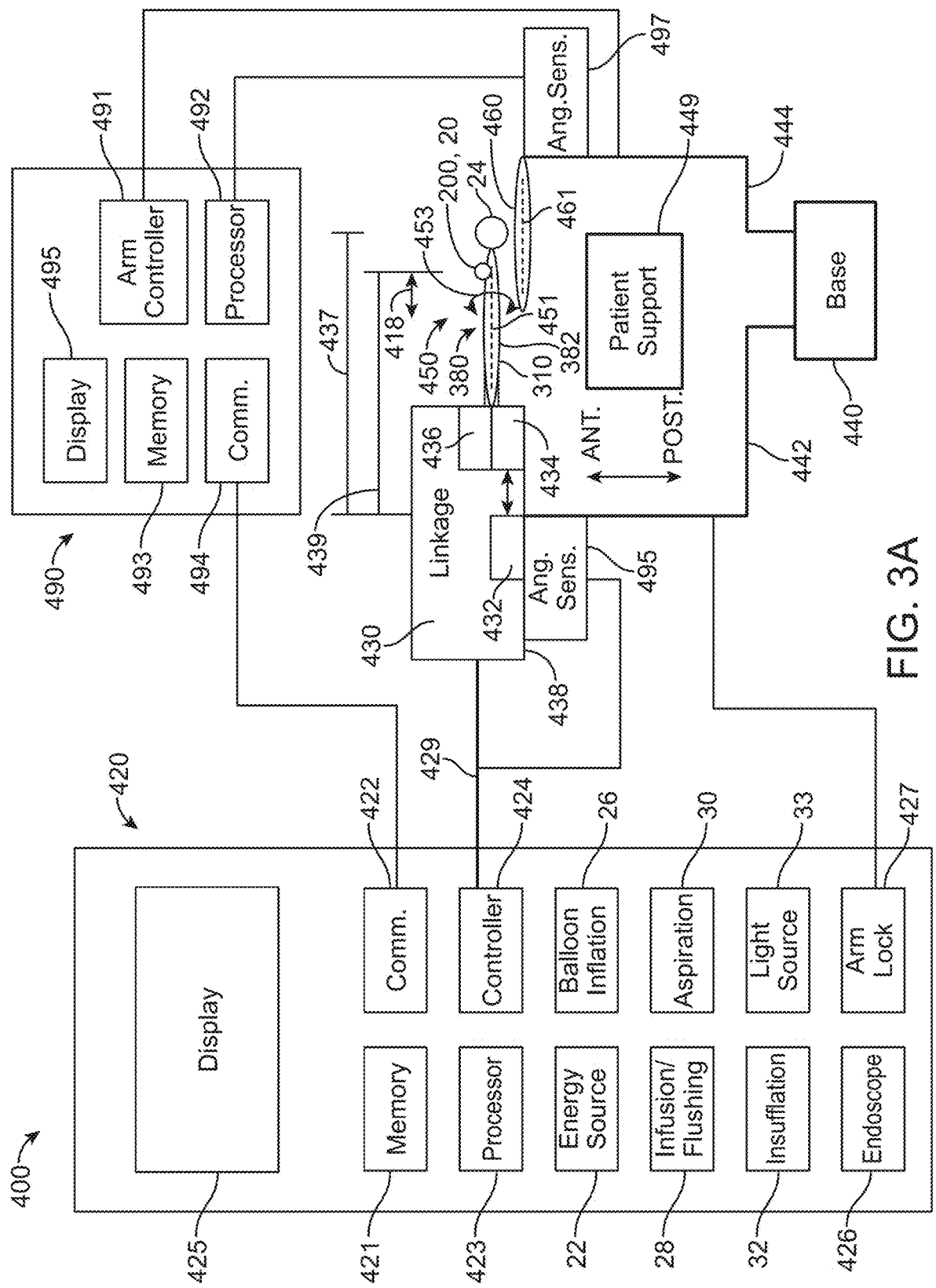
FIGS. 3A and 3B show a system to treat a patient in accordance with embodiments.
Figure 3B:
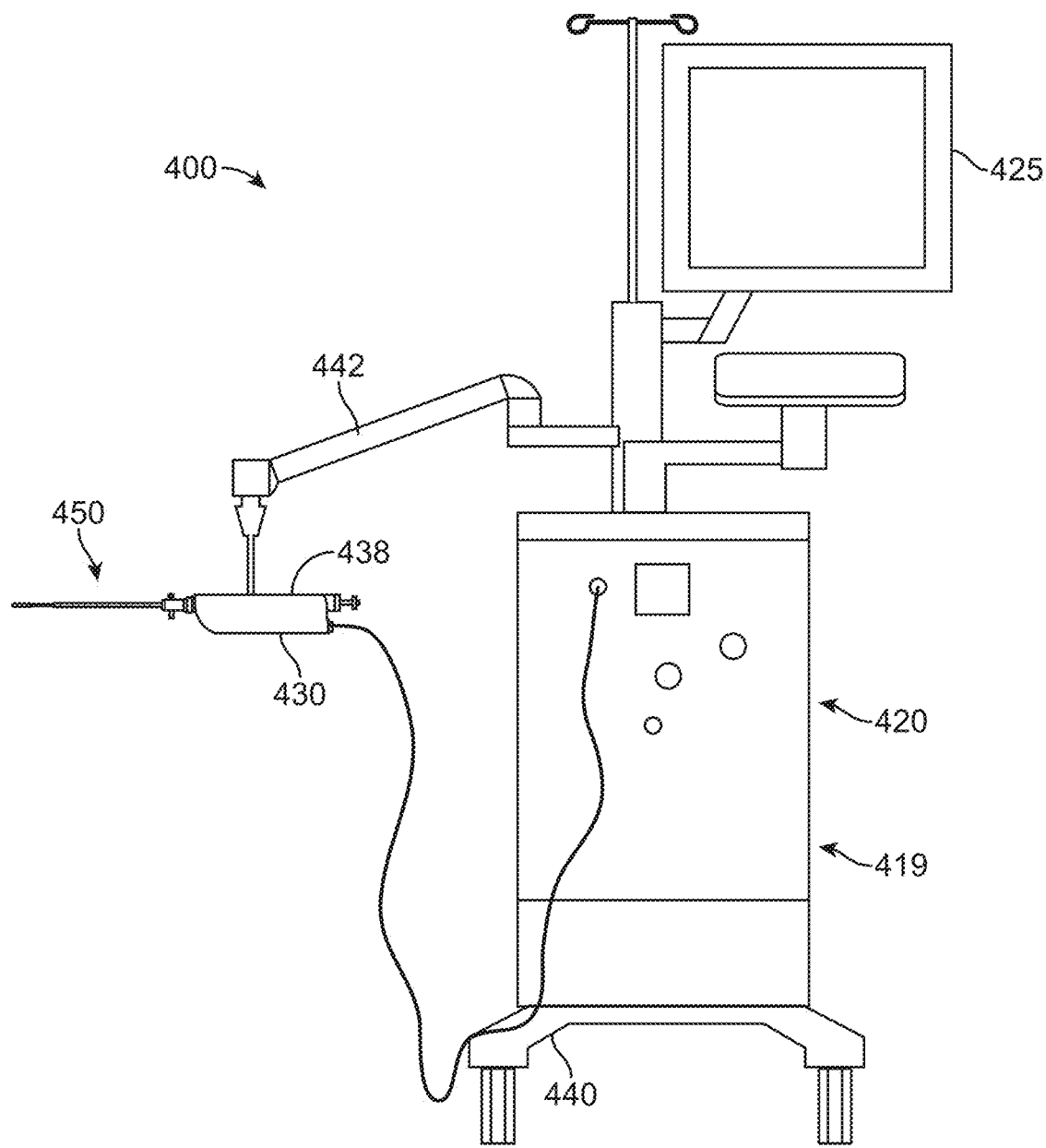

FIGS. 3A and 3B show a system to treat a patient in accordance with embodiments. The system 400 comprises a treatment probe 450 and may optionally comprise an imaging probe 460. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460, in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be used to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the treatment probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging system 490. The console 420 comprises components of an endoscope 35 that is coupled to anchor 24. Infusion flashing control 28 is coupled to probe 450 to control infusion and flushing. Aspiration control 30 is coupled to probe 450 to control aspiration. Endoscope 426 can comprise components of console 420 and an endoscope insertable with probe 450 to treat the patient. Arm lock 427 of console 420 is coupled to arm 422 to lock the arm 422 or to allow the arm 422 to be freely movable to insert probe 450 into the patient.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 437 to the anchor 24. The substantially fixed distance 437 between the anchor 24 and the fixed first portion 432 of the linkage allows the treatment to be accurately placed. The first portion 424 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle around the elongate axis. During treatment of the patient, a distance 439 between the treatment region 20 and the fixed portion of the linkage varies with reference to anchor 24. The distance 439 adjusts in response to computer control to set a target location along the elongate axis of the treatment probe referenced to anchor 24. The first portion of the linkage remains fixed, while the second portion 434 adjusts the position of the treatment region along the axis. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490 comprises a memory 493, communication circuitry 494 and processor 492. The processor 492 in corresponding circuitry is coupled to the imaging probe 460. An arm controller 491 is coupled to arm 444 to precisely position imaging probe 460.

Figure 4A:
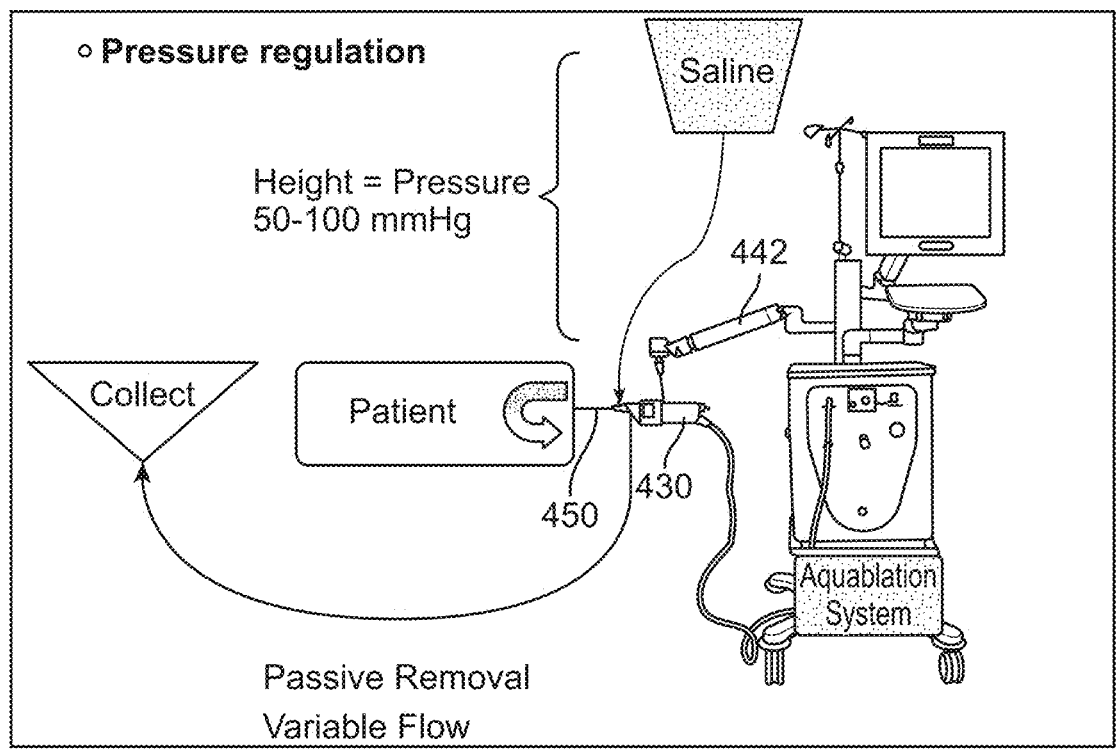
FIG. 4A shows pressure regulation of the surgical site with a substantially constant pressure and variable flow, in accordance with embodiments.

FIG. 4A shows pressure regulation of the surgical site with a substantially constant pressure and variable flow. The saline bag is placed at a height to provide substantially constant pressure regulation. The bag of saline can be placed at a height corresponding to about 50 to 100 mm of Mercury (hereinafter "mmHg"). The saline bag is coupled to the irrigation port as described herein. A collection bag is coupled to one or more of the irrigation port, the aspiration port, or the suction port as described herein. The collection bag collects tissue removed with the waterjet ablation probe 450 as described herein.

Figure 4B:
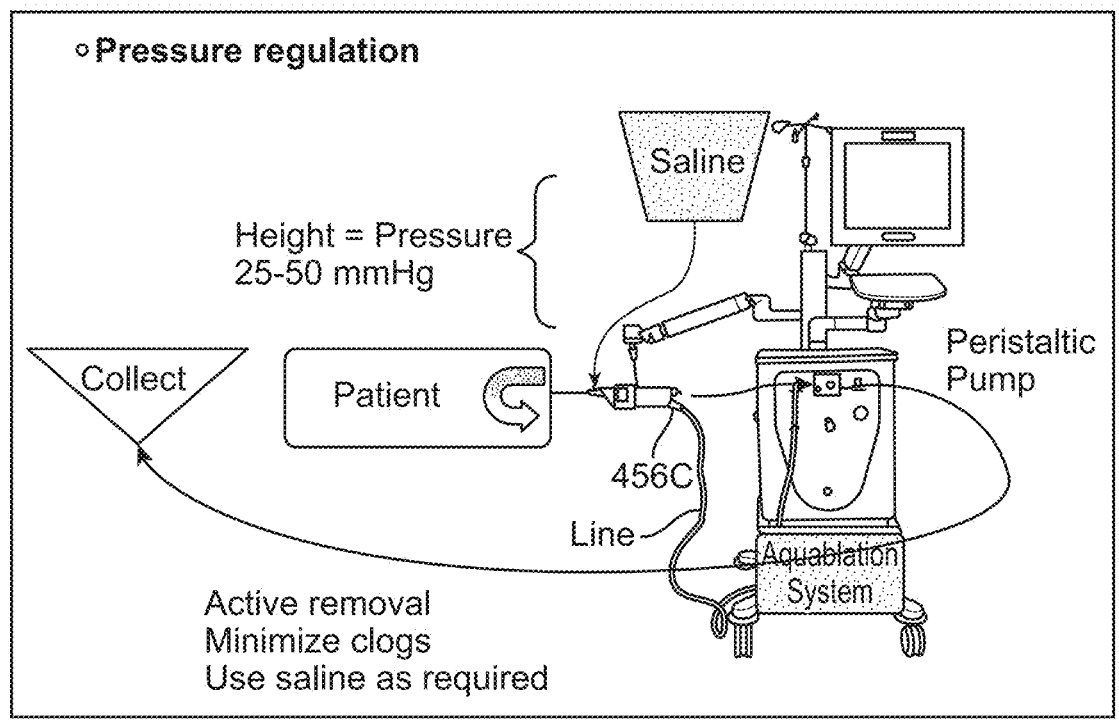
FIG. 4B shows flow regulation of the surgical site with a pump providing a substantially fixed fluidic flow and a substantially constant pressure, in accordance with embodiments.

FIG. 4B shows flow fluidic regulation of the surgical site with a pump providing a substantially fixed fluidic flow. A pump removes fluid from the surgical site at a substantially fixed flow rate. The pump may comprise a peristaltic pump, for example. The pump is configured to remove fluid at substantially the same rate or greater than the Aquablation saline flow rate, in order to inhibit pressure build up at the surgical site. The peristaltic pump can be coupled to the aspiration port of the manifold comprising tissue removal port 456C as described herein, for example. Providing the pump having the flow rate that is at least the flow rate of the tissue ablation jet provides improve suction as ablated tissue that might otherwise block the tissue removal openings and channel can be subjected to greater amounts of pressure when the pump maintains the substantially fixed flow rate in order to remove the material that would otherwise block the channel.

The irrigation flow from the saline bag may remain open in order to provide at least two functions: 1) maintain pressure based on the height of the saline bag; and 2) provide a safety check valve in case the peristaltic pump is not functioning correctly as visually a person would see flow entering the bag as a pink color.

In alternate embodiments, the flow of the pump comprises a variable rate in order to provide a substantially constant pressure within the patient near the surgical site. The active sensing of pressure of the treated organ and variable flow rate of the pump may comprise a closed loop pressure regulation system. The pump can be coupled to a sensor such as a pressure sensor, and the flow rate varied to maintain substantially constant pressure. The pressure sensor can be located in one or more of many places such as on the treatment probe, within the aspiration channel of the probe, in a recess of an outer surface the probe, on an inner surface of the probe coupled to the surgical site, or near the inlet to the pump on the console for example.

Figure 5A:
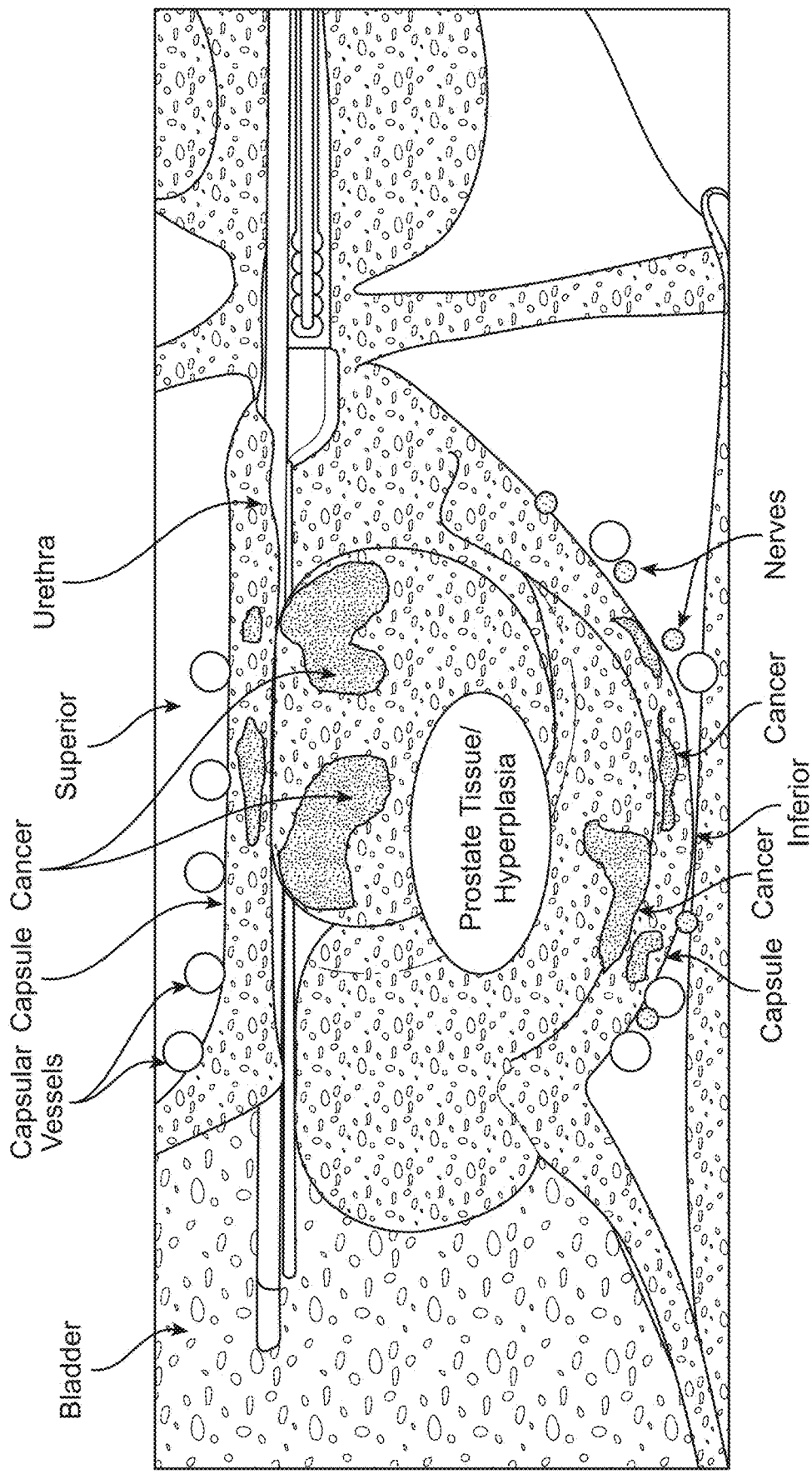
FIG. 5A shows an organ suitable for incorporation in accordance with many embodiments.

FIG. 5A shows an organ suitable for incorporation in accordance with embodiments. The organ may comprise one or more of many organs as described herein, for example, the prostate. In many embodiments the organ comprises a capsule and tissue contained within the capsule and capsular vessels and nerves located on an exterior of the capsule, for example. In many embodiments the organ comprises a prostate. The prostate may comprise hyperplasia such as benign prostate hyperplasia or cancer and combinations thereof, for example. In many embodiments the hyperplasic tissue may comprise tissue located within the patient in which the cancer may not have been detected. In many embodiments capsular vessels and nerves extend along an exterior surface of the prostate. In many embodiments the hyperplasic tissue can be located superiorly on the prostate. In the many embodiments the hyperplasic tissue may comprise tissue of unknown specificity with respect to whether the tissue comprises cancerous tissue or benign tissue.

Figure 5B:
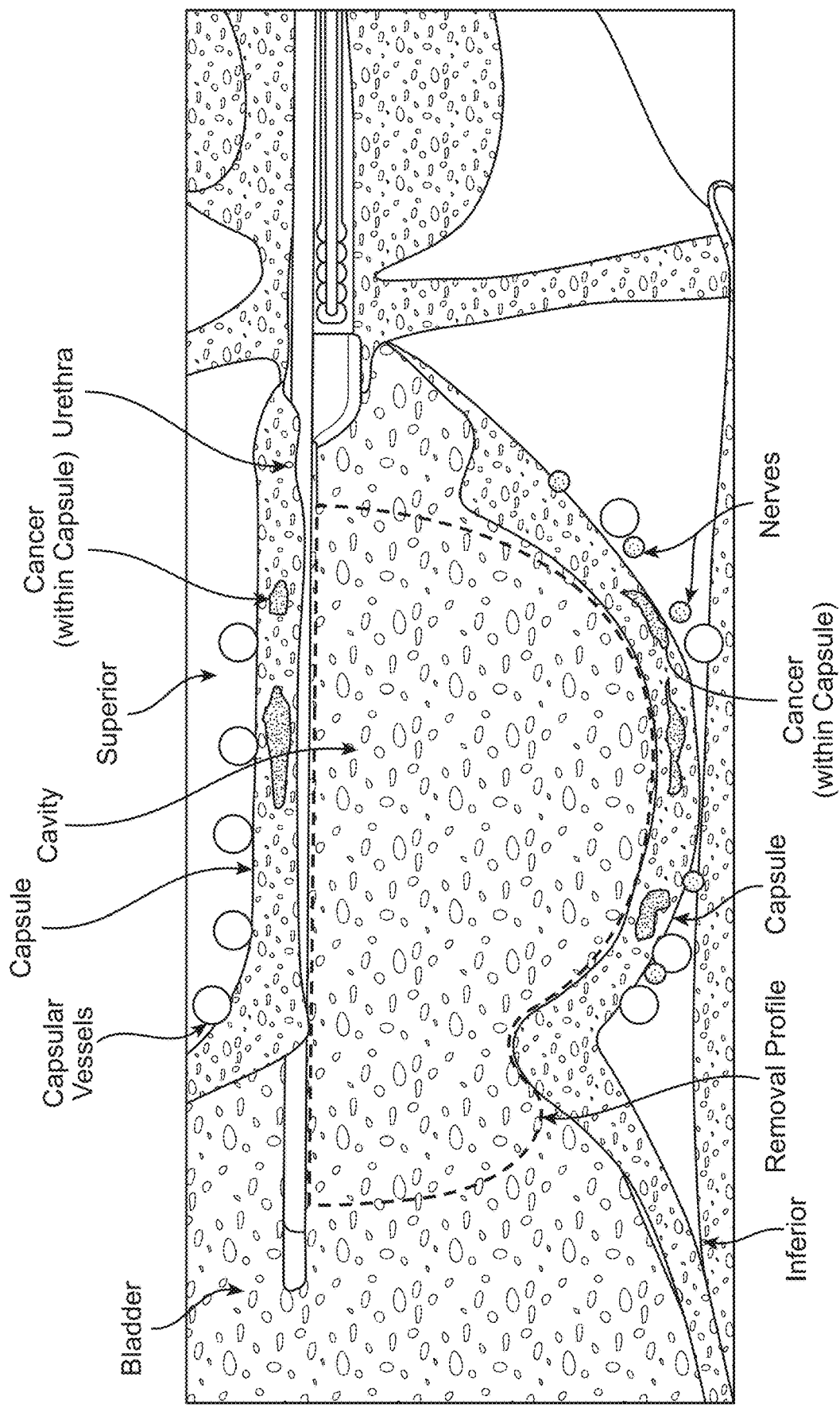
FIG. 5B shows the prostate of FIG. 5A treated with an apparatus in accordance with many embodiments.

FIG. 5B shows the prostate of FIG. 5A treated with an apparatus in accordance with embodiments. In many embodiments the tissue of the prostate is removed in accordance with a tissue removal profile. The tissue removal profile may comprise of predetermined tissue removal profile based on image-guided tissue removal as described herein, for example. Alternatively the tissue removal profile may comprise of removal profile of tissue removed with a handheld tissue removal apparatus. In many embodiments the tissue of the organ, such as the prostate, is removed to within the capsule in order to decrease the distance from the tissue removable profile to the exterior of the capsule, for example.

In many embodiments a tissue treatment apparatus, such as a catheter having an expandable support, is placed within the organ in order to engage the remaining tissue that defines the removal profile and the capsule with an expandable support.

In many embodiments the tissue within the organ is removed such that the capsule of the organ, such as the prostate, remains intact which has the advantage of retaining the integrity of the capsule or vessel's nerves which may extend around an exterior surface of the capsule. In many embodiments this removal of the capsular tissue is inhibited in order to retain the integrity of the capsule and the corresponding tissue structures such as capsular vessels and/or nerves. The tissue removal profile may define a cavity corresponding to the removed tissue of the organ such as the prostate. In many embodiments a portion of the tissue near the capsule may comprise tissue, such as cancerous tissue or tissue identified as having a probability of being cancerous tissue, such as hyperplasic tissue in the superior portion or other portion of the organ.

Figure 6:
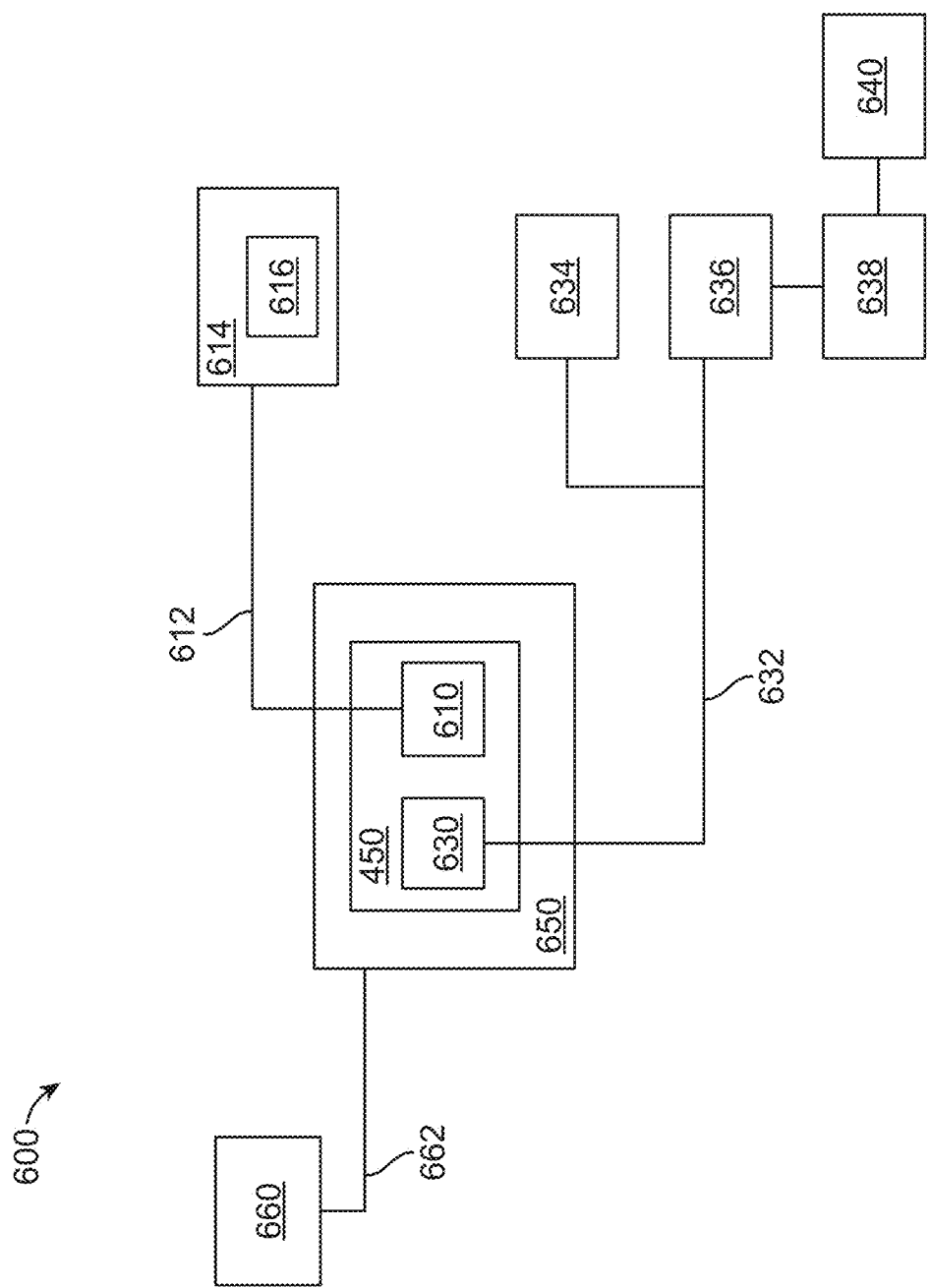
FIG. 6 shows an apparatus to remove intact cells from a surgical site of a patient, in accordance with embodiments.

FIG. 6 shows an apparatus 600 to remove intact cells from a surgical site of a patient. The apparatus 600 may comprise one or more components of system 10 or system 400 as described herein, for example. The apparatus comprises a probe 650 that may be inserted to the surgical site. The probe comprises a nozzle 610 configured to provide a fluid stream to the surgical site to fragment tissue, and a port 630 configured to receive the tissue from the surgical site. The port is coupled to a filter 636 configured to receive the tissue comprising the intact cells from the surgical site. The filter may be further coupled to a collection apparatus 638 that houses the filter. Optionally, the collection apparatus may be coupled to an external vacuum pump 640 configured to provide additional negative pressure to help assist in the collection of the fragmented tissue.

The apparatus may further comprise a first channel 612 extending from a fluid source 614 to the nozzle to generate the fluid stream, and second channel 632 extending from the port toward the filter to transport the fragmented tissue away from the surgical site. The fluid source may comprise a first pump 616 connected to the first channel, configured to drive the fluid stream from the fluid source to the nozzle. The second channel may be further coupled to a second pump 634, configured to transport the fragmented tissue from the port to the filter.

In some embodiments, the flow rate of the first pump and the flow rate of the second pump are configured to be substantially similar, such that the tissue fragments and fluid are removed at a rate similar to the rate of the fluid injected into the surgical site with the fluid stream.

The nozzle and the port may be configured to provide a closed surgical site 650 within the patient, such that a constant volume of fluid is maintained within the surgical site. The apparatus may further comprise a fluid reservoir 660 and a channel 662 extending between the fluid reservoir and the surgical site. The fluid reservoir can help to accommodate any differences between the flow rate of the first pump and the flow rate of the second pump, so that the volume of the closed surgical site remains substantially constant and pressure build-up at the surgical site is inhibited. The fluid reservoir may provide a safety check valve in case one or more of the first or second pump is not functioning correctly, for example as when a tissue fragment is blocking the port.

Work in relation to embodiments suggests that the substantially fixed pressure of the closed surgical site can treat the intact cells gently and allow the fragment tissue to flow to the collection device comprising the filter.

Figure 7A:
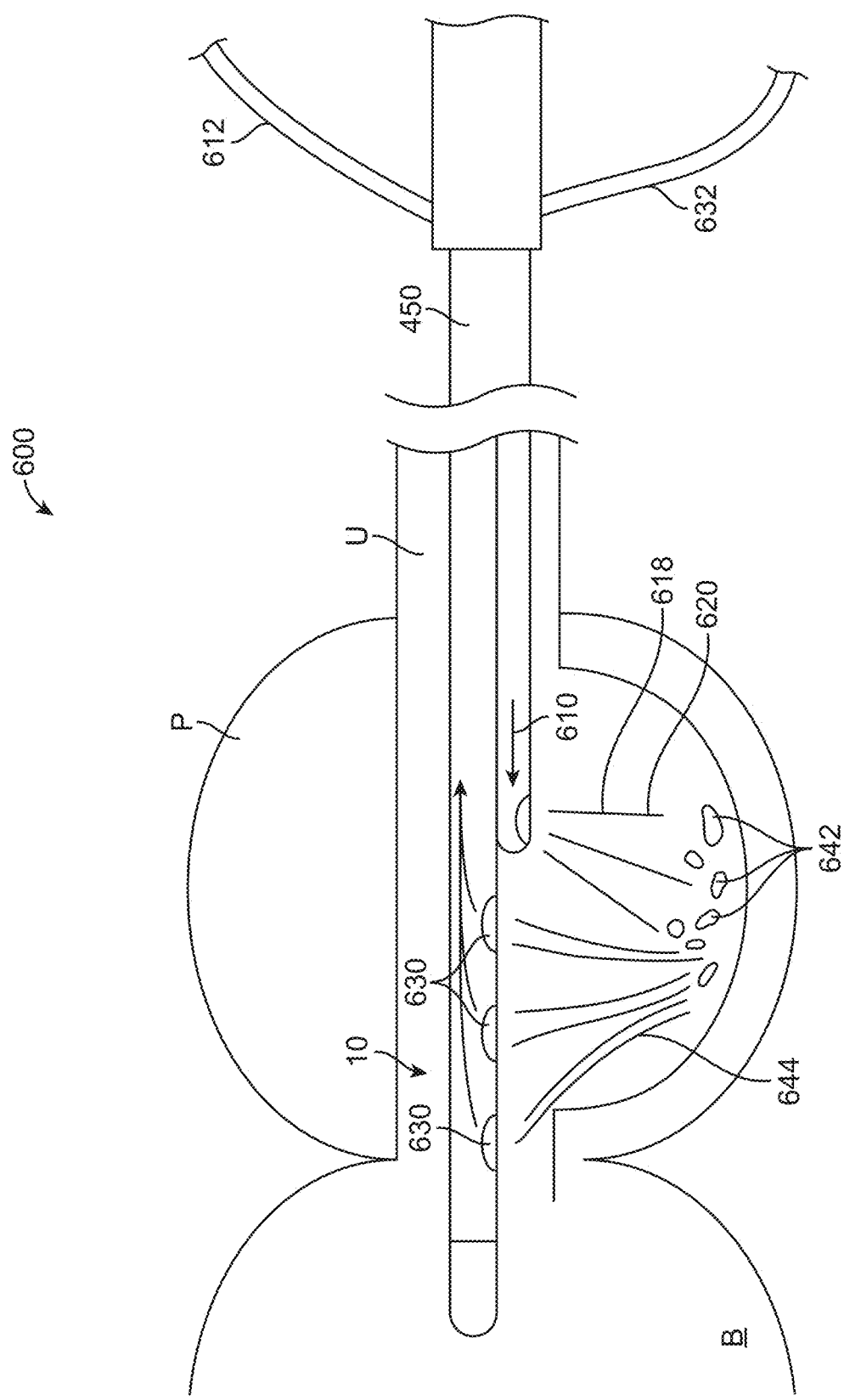
FIG. 7A shows structure of the apparatus of FIG. 6.

FIG. 7A shows an exemplary probe in accordance with embodiments of the apparatus as described herein such as apparatus 600. In the exemplary embodiments of FIG. 7A, the apparatus may be used to remove intact cells from a prostate P of a patient. The apparatus comprises a prostatic tissue debulking device 10 as described herein, wherein the device comprises a probe 450 that may be inserted into the male urethra U to a surgical region within the prostate located immediately distal to the bladder B of the patient. The probe comprises a nozzle 610 to deliver a fluid stream 618 to the surgical region, and thereby remove a plurality of tissue fragments 642 from the prostate. The probe also comprises one or more ports 630 to receive the slurry 644 from the surgical site, where the slurry comprises fluid from the fluid stream and tissue fragments removed from the prostate. The fluid stream may be delivered to the nozzle through a first channel 612, which is connected to a fluid source comprising a first pump. The slurry may be transported from the surgical site through a second channel 632, to a filter configured to receive the slurry.

The nozzle may comprise an inner restricted diameter corresponding to a diameter of the fluid stream released from the nozzle. The inner restricted diameter of the nozzle may range from about 25 um to about 500 um, preferably within a range from about 100 um to about 200 um, more preferably from 120 um to 150 um.

The fluid stream may comprise one or more of a liquid or a gas. A liquid fluid stream may comprise one or more of water or saline, for example. A liquid fluid stream may be configured to exit the nozzle in the form a liquid ablation jet 620, causing cavitations in the prostate tissue and dissociating the tissue into a plurality of fragments.

Figure 7B:
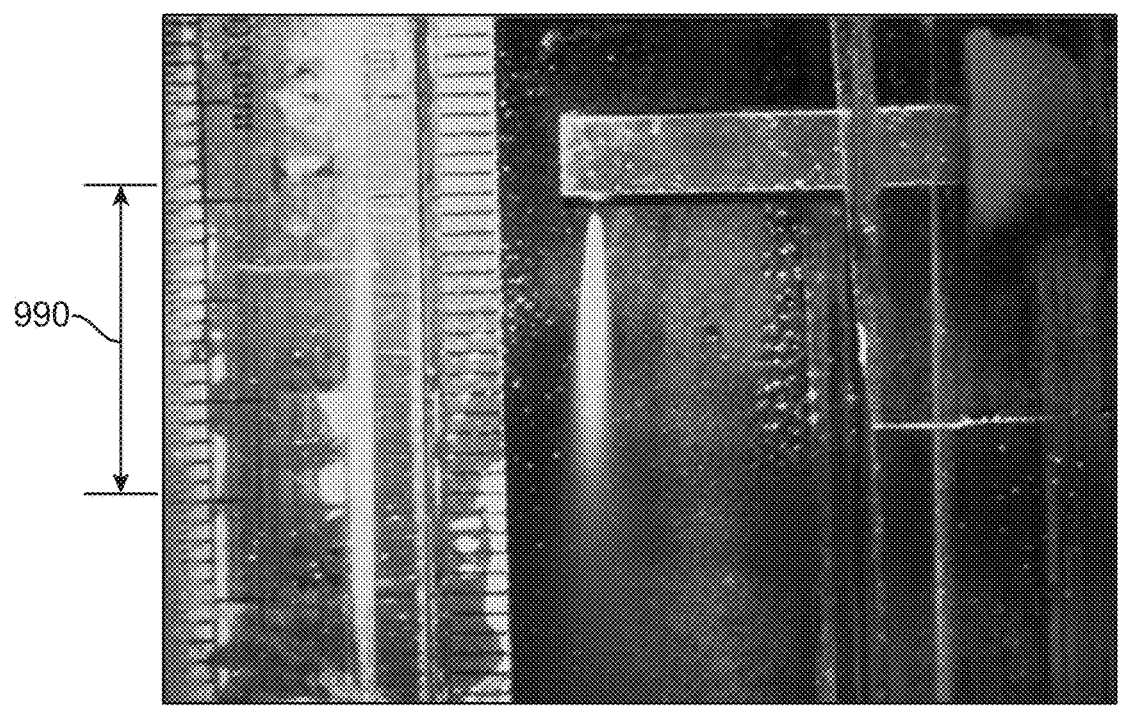
FIG. 7B shows an ablative flame visible to the human eye, in accordance with embodiments.

FIG. 7B shows an ablative flame visible to the human eye, in accordance with embodiments.

Figure 7C:
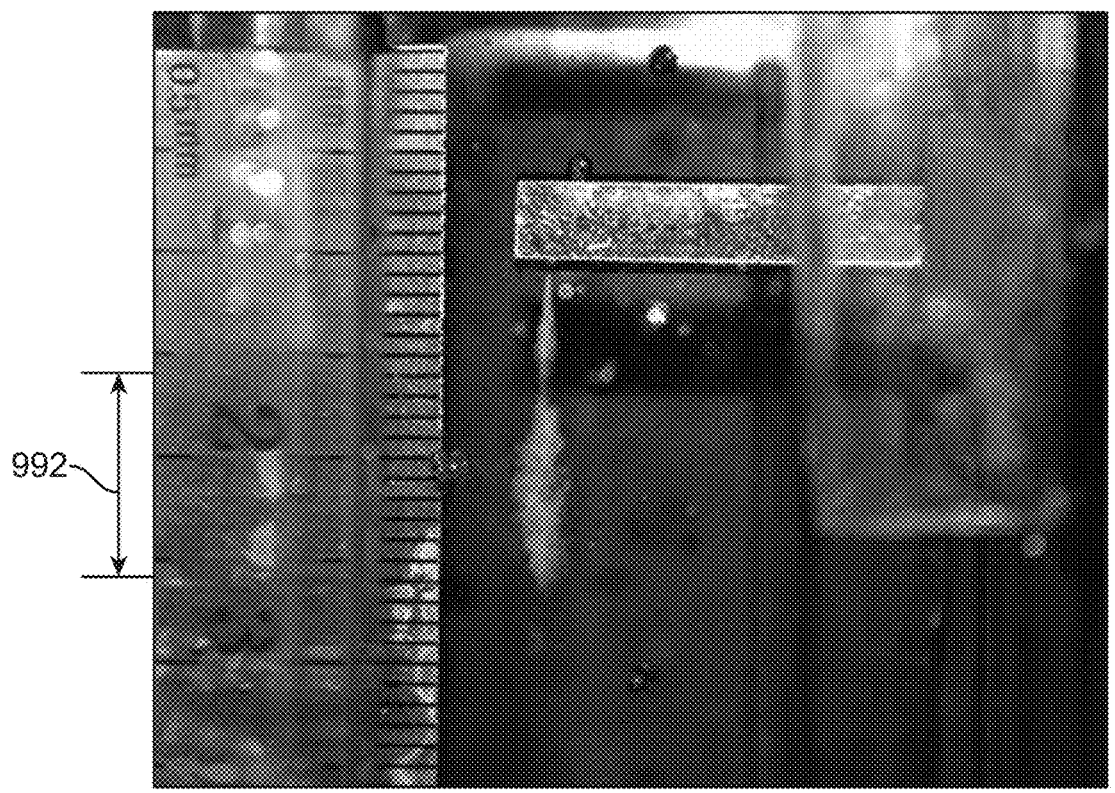
FIG. 7C shows a high speed image of the ablative flame as in FIG. 7B.

FIG. 7C shows a high speed image of the ablative flame as in FIG. 7B. The image was taken at a speed of about 1/400 of a second.

The data of FIGS. 7B and 7C show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in an non-cutting configuration as shown in FIG. 7C, in order to allow the shedding cloud to substantially form prior to the cloud striking tissue. This divergence of the shed cloud to a larger cross sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination of the high velocity fluid that defines the cavitations striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue and can be located on the probe to provide improved tissue resection.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

Figure 7D:
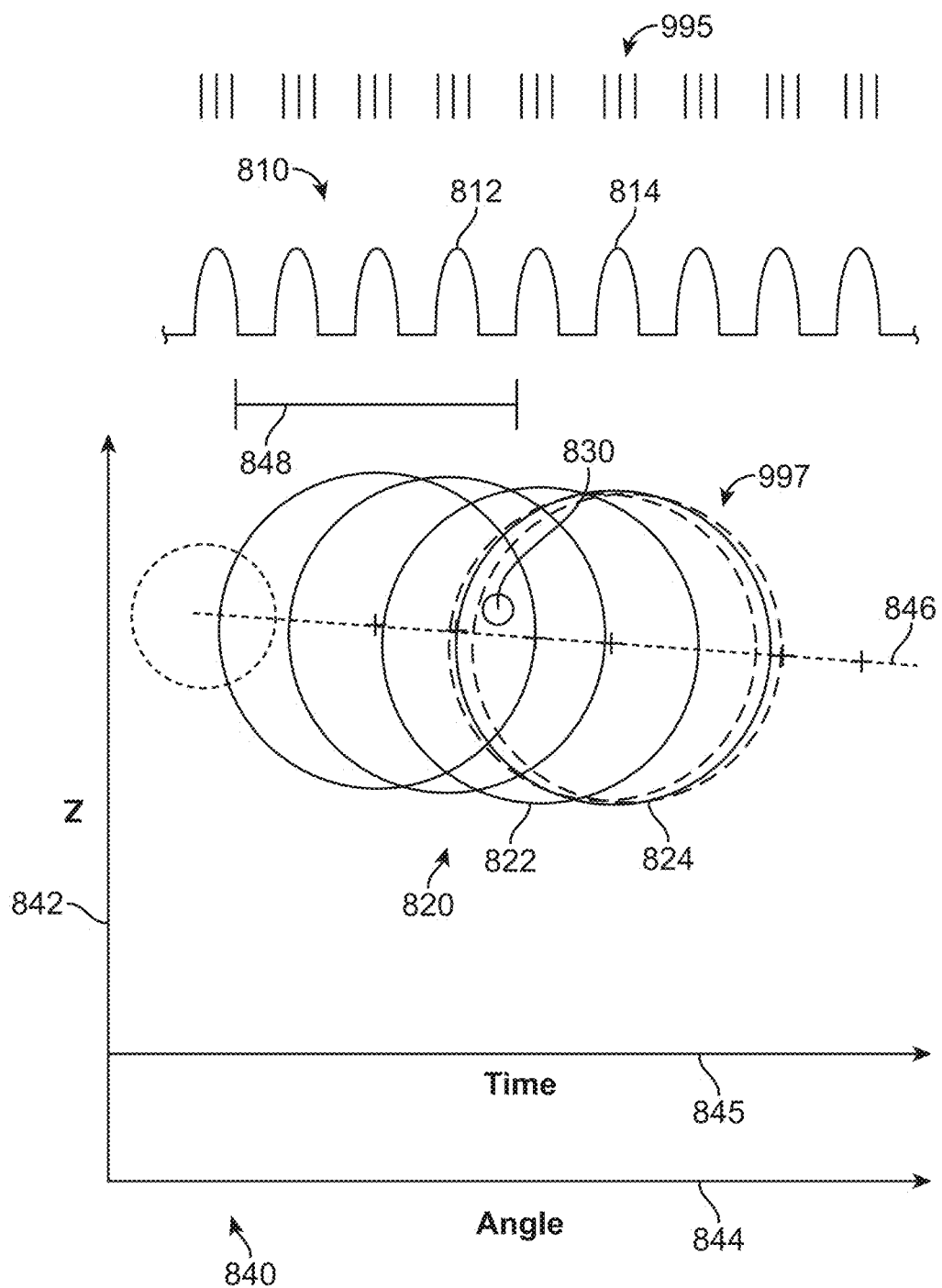
FIG. 7D shows a plurality of shedding pulses and sweeping of the ablative jet to provide smooth and controlled tissue erosion at a plurality of overlapping locations in accordance with embodiments.

The shedding frequency and size 848 of the cloud shed from the jet can be used to provide tissue ablation in accordance with embodiments as shown in FIG. 7D. The shedding frequency can be combined with the angular sweep rate of the probe around the longitudinal axis to provide overlap of the locations where each cloud interacts with the tissue.

FIG. 7D shows a plurality of shedding pulses 995 and sweeping 820 of the ablative jet to provide smooth and controlled tissue erosion at a plurality of overlapping locations 997 at time 845, angle 844, and z position 842 of the jet, in accordance with embodiments. This shedding frequency can be substantially faster than the pump frequency 810, when a pump is used, such that a plurality of shedding clouds 995 are provided for each pulse 814 of the pulsatile pump. The sweep rate of the probe along path 846 can be related to shedding frequency to provide improved tissue removal, for example with the shedding clouds configured to provide overlapping pulses 822, 824, at location 830.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 KHz.

Although pulses of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St=(Fshed)*(W)/U$$

where Fshed is the shedding frequency, W is the width of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the probes as described herein. The nozzle may be arranged with the port in order to immerse the liquid jet in a liquid in order to generate a plurality of shedding pulses with the jet immersed in the liquid.

The flow rate of the fluid stream may range from about 10 ml/min to about 500 ml/min, preferably within the range from about 50 ml/min to about 250 ml/min. A fluid ablation jet exiting the nozzle may have a longitudinal velocity ranging from about 0.01 mm/sec to about 50 mm/sec, preferably within the range from about 0.1 mm/sec to about 5 mm/sec.

The probe may be configured such that the fluid ablation jet rotates during the tissue removal procedure, such that tissue samples can be collected from various locations within the surgical site. The rotation of the fluid ablation jet during the course of tissue removal may be in the range from 0 to 360 degrees, preferably within the range of about 30 degrees to about 300 degrees. The angular velocity of the jet around the longitudinal axis of the probe may range from about 10 deg/sec to about 2000 deg/sec, preferably within the range of about 180 deg/sec to about 900 deg/sec. The longitudinal length of the profile of the tissue removal procedure may range from about 0.1 mm to about 300 mm, preferably within the range of about 1 mm to about 70 mm.

EXPERIMENTAL

Figure 7E:
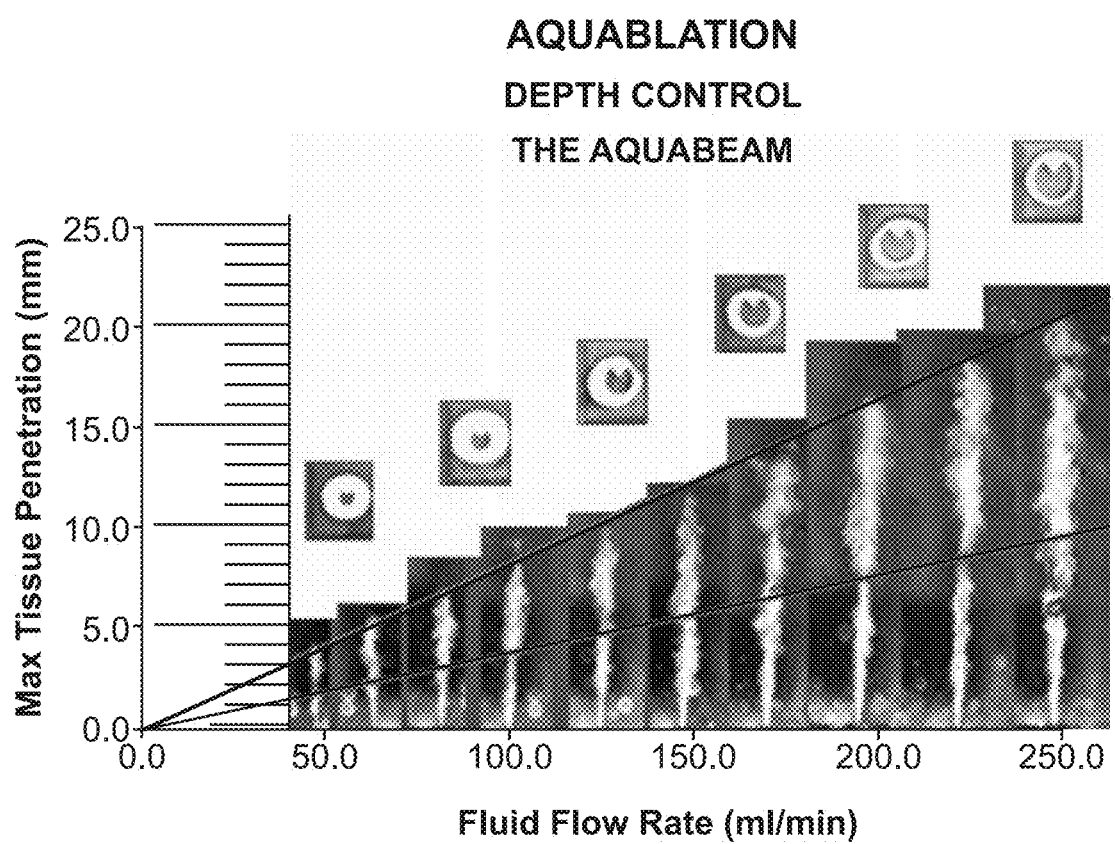
FIG. 7E shows maximum tissue penetration depth of cutting and flow rate through a nozzle in accordance with embodiments.

FIG. 7E shows maximum tissue penetration depth of cutting and flow rate through a nozzle in accordance with embodiments. The maximum penetration depth corresponds substantially to the length of the cavitation bubbles of the jet comprising the "cold" aquablation flame. The maximum tissue penetration depth of ablation corresponds directly to the flow rate and in many embodiments is linearly related to the flow rate.

The inset of FIG. 7E shows cut potato as a model of prostate BPH, in accordance with embodiments. The maximum penetration depth of potato corresponds closely to the maximum cut depth of BPH. The potato is shown cut with 10 different flow settings corresponding to rates within a range from about 50 ml/min to about 250 ml/min with a nozzle and rotating probe as described herein. The maximum penetration depth ranges from about 4 mm at 50 ml/min to about 20 mm at about 250 ml/min.

In many embodiments, the cavitation cloud growth and length comprises a function of flow rate, which is proportional to the injection pressure and vice versa, for an appropriately configured nozzle as described herein. As the pressure increases, the maximum erosive radius appears to increase linearly, which is shown as the maximum penetration depth of FIG. 7E.

High velocity cavitating jets can be created by using an known high pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related cavitation can occur inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aquablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the devices nozzle, either by translating the nozzle along the anterior-posterior direction or by rotating the nozzle up to 180 degrees, for example.

As vapor cavity formation and its erosive strength is a function of both injection pressure and the flow dynamics, the depth of material can be controlled by configuring the pressure as well as nozzle geometry. A greater injection pressure will result in a faster exit velocity. As discussed herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the Aquablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, Aquablation as described herein is capable of removing the excess tissue growth, e.g. BPH, with inhibited removal and damage of arteries and veins. The pressure pulses and microjets caused by cavitation exceed the threshold energy required to erode the soft tissue growth, and may cause minimal damage to other structures like vessels which have a much higher threshold energy. Repeated and concentrated pressure pulses and microjets may cause fatigue stress on the vasculature and result in bleeding, but the Aquablation system algorithm and treatment instructions as described herein are configured designed to inhibit such damage.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Aquablation as described herein takes advantage of this phenomenon. The naturally self-limiting erosive radius and unique ability to precisely ablate tissue with a low damage threshold energy while minimizing damage to nearby structures with a more dense cellular structure, such as arteries, make Aquablation as described herein a useful surgical tool for treating BPH. Coupled with the nearly isothermal property of cavitation as described herein, which can mitigate collateral damage and provide improved healing and an improved safety profile.

Figure 7F:
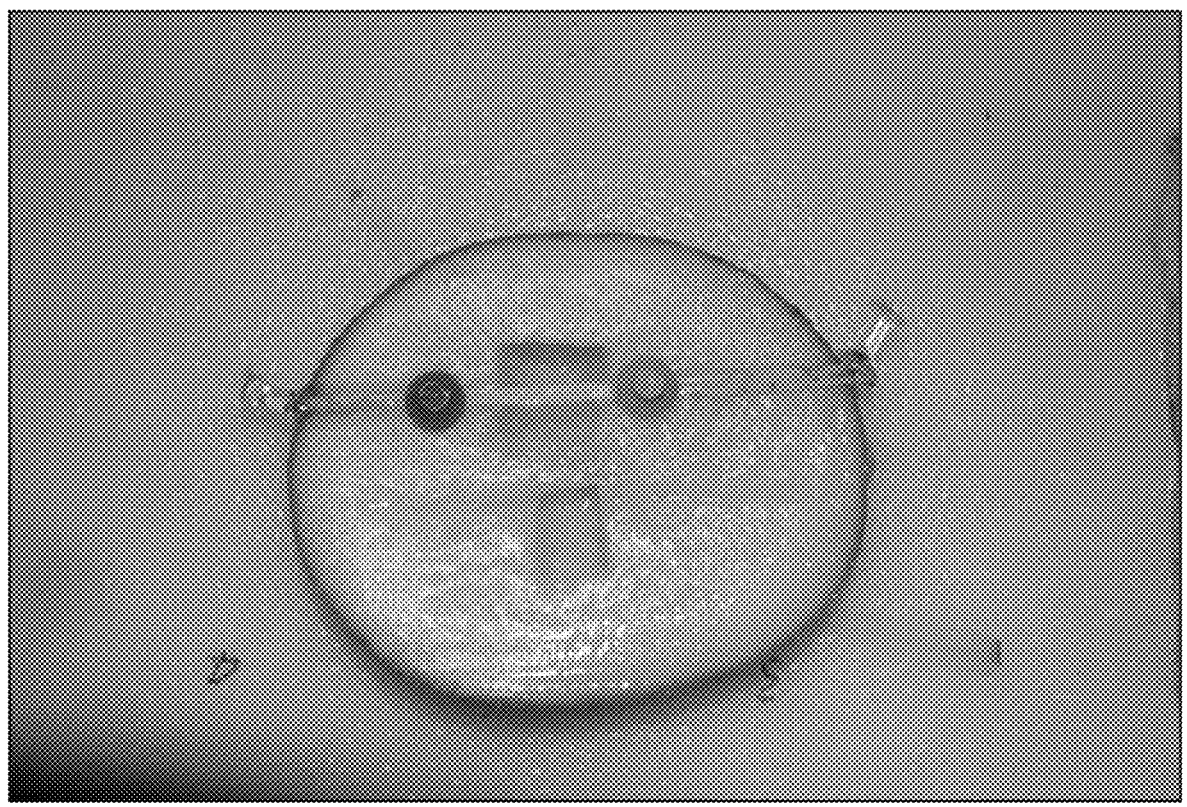
FIG. 7F shows selective removal of potato with a porcine blood vessel positioned over the incision of the potato as a model for selective removal of tissue.

FIG. 7F shows selective removal of potato with a porcine blood vessel positioned over the incision of the potato as a model for selective removal of tissue. The porcine blood vessel was placed on the potato prior to the incision, such that the porcine blood vessel was exposed to the water jet with cavitation in order to remove the potato. Aquablation resected the soft potato tissue model, which is a close proxy for the benign tissue growth seen in BPH, without causing severe damage to the porcine vessel.

While the embodiments of FIG. 7A describes an apparatus to remove cells from prostate tissue, one of skill in the art will appreciate that the apparatus may be adapted to remove cells of other tissues of an organ.

Figure 8:
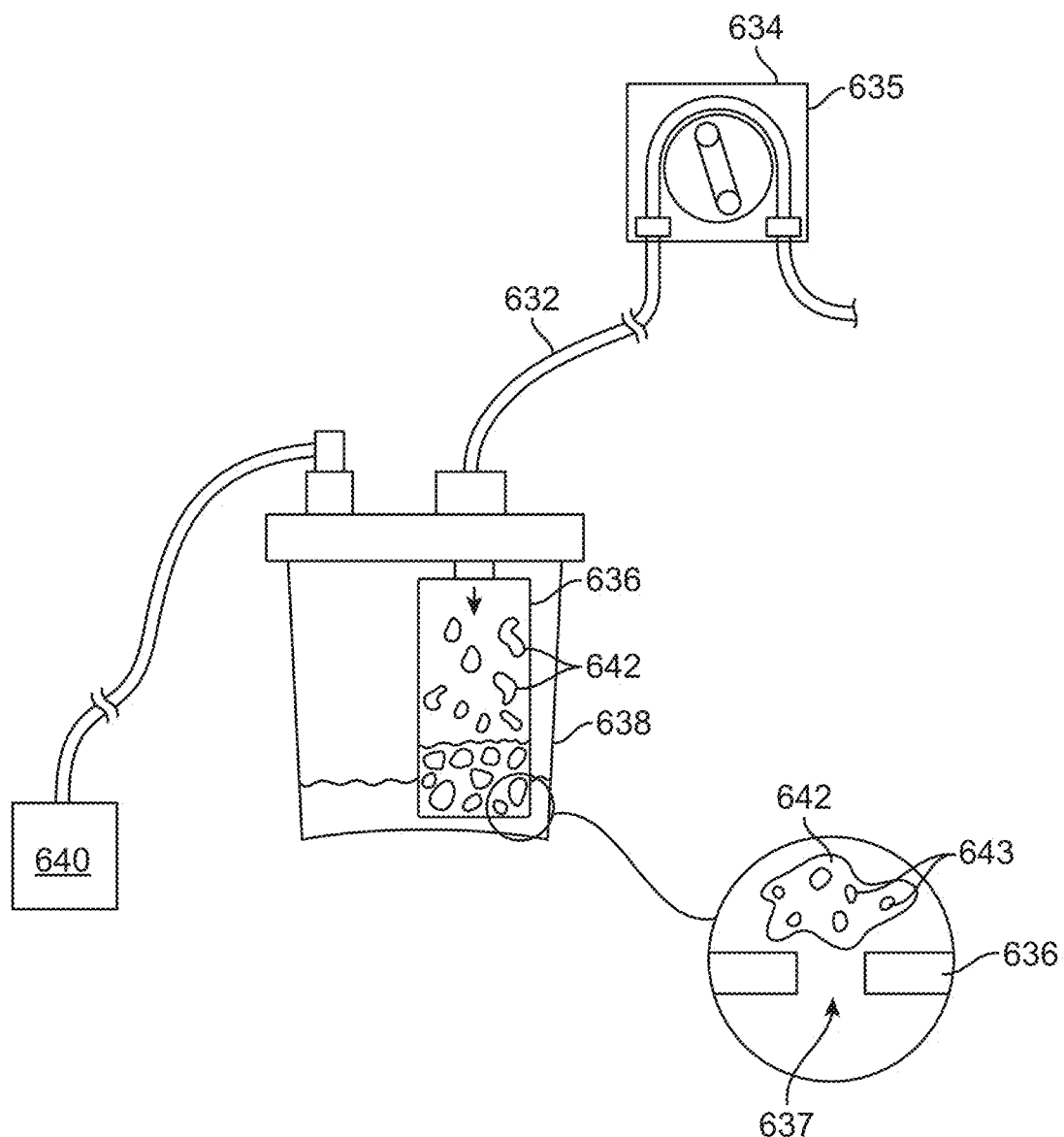
FIG. 8 shows a filter configured to receive the fragmented tissue samples comprising the intact cells, in accordance with embodiments.

FIG. 8 shows a filter 636 configured to receive the fragmented tissue 642 samples comprising the intact cells, in accordance with embodiments. The filter is coupled to the surgical site through the second channel 632. The second channel is also coupled to a second pump 634 configured to transport the fragmented tissue from the port to the filter. The second pump may comprise a peristaltic pump 635 that moves the tissue samples by positive displacement, wherein the peristaltic pump may be configured to pump at a rate substantially similar to the rate of first pump driving the fluid stream, for example similar to within about 10%, for example 5% or less. Alternately, the second pump may comprise a vacuum pump that moves the tissue samples by negative pressure, wherein the vacuum pump may be configured with a trap to main the sterility of the samples and of the pump mechanism.

The filter may comprise a plurality of pores 637 having a plurality of pore sizes. The pore sizes may be dimensioned to be larger than the dimensions of the intact cells 643 of the tissue being removed, so that the tissue fragments comprising the cells may be collected with the filter.

The filter may be further coupled to a collection apparatus 638 that houses the filter, wherein the filter is removable and replaceable. Optionally, the collection apparatus may be coupled to an external vacuum pump 640 configured to provide additional negative pressure to help assist in the collection of the fragmented tissue. Once tissue samples have been collected in the filter, the filter may be removed from the collection apparatus and sent for the harvesting of the intact cells disposed in the tissues, or for other procedures as described herein.

The removed tissue comprising intact cells may be analyzed for diagnostic purposes, such as for the diagnosis of cancer. For example, removed prostate tissue may be analyzed for the diagnosis of prostate cancer (PCa) or benign prostate hyperplasia (BPH). Tissue fragments may be analyzed via histology or immunohistochemistry for the presence of cancer. Further, intact cells within the tissue fragments may be harvested and used for cellular analysis to detect cancer. Studies have shown that prostate stem cells display different biomarkers depending on whether they are normal, BPH, or PCa stem cells (Prajapati et al., Biomed Res Int 2013; 2013:107954). Cells may be separated from the tissue fragments using methods well known in the art, such collagenase digestion of tissue followed by repeated centrifugation to release and separate cells. Separated cells may be expanded in vitro, then analyzed for biomarker expression via immunocytochemistry or flow cytometry, as is well known in the art. One or more of the following biomarkers for prostate stem cells may be analyzed: CD44, p63, Sca-1, CD133, p27Kip1, CD117, Trop2, CD49f, AR, CK5, 8, PSCA. Prostate stem cells may be identified as normal, for example when they display the profile p63(+)AR(−)CK5(+)8(−), or they may be identified as BPH, for example when they display the profile p63(+)AR(+)CK5(+)8(−)PSCA$^{hi}$, or they may be identified as prostate cancer, for example when they display the profile p63(−)AR(+)CK5(−)8(−)PSCA$^{hi}$. Identification of the cells as normal, BPH, or PCa stem cells can help diagnose BPH or PCa in the tissue sample, and help decide the subsequent course of treatment for the patient.

The removed tissue comprising intact cells may also be processed to generate cell lines for use in research and therapeutics. For example, prostate stem cells may be harvested from resected prostate tissue to generate pluripotent stem cell lines for potential use in cancer research and cell-based therapeutics. Cells may be harvested from the tissue fragments and expanded in vitro, as described herein. Cells displaying cell-surface markers for stem cells, such as CD44, integrin α2β1, CD133, and CK6a, may be sorted via immunomagnetic sorting or fluorescence-activated cell sorting (FACS), as is well-known in the art. Sorted cells may be expanded in vitro and subsequently verified for their expression of target biomarkers, such as via reverse-transcriptase polymerase chain reaction (RT-PCR) and gel electrophoresis, western blotting, immunocytochemistry, or flow cytometry. The sorted cells may be further evaluated for their ability to differentiate in vitro or in vivo. Some studies have shown that pluripotent stem cell lines may be derived from resected human prostate tissue, with potential uses in studies of prostatic disorders as well as in regenerative medicine (Prajapati et al., J Stem Cell Res Ther 2014; 4:1).

An apparatus for the removal of tissue comprising intact cells as described herein may be further configured to enable the removal of tissue fragments from localized zones within the surgical site.

Figure 9C:
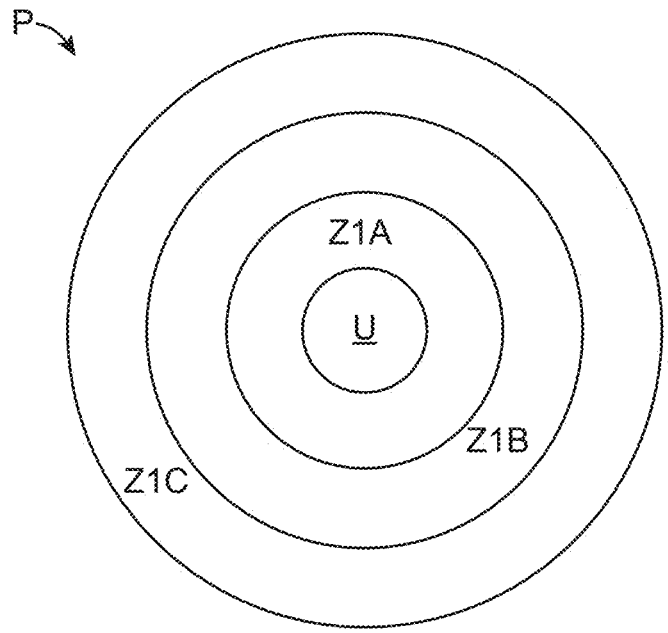
Figure 9D:
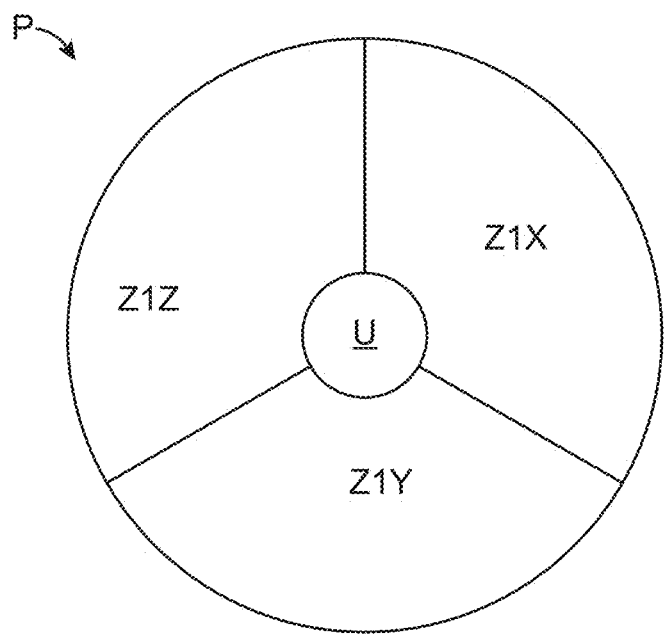

FIGS. 9A-9D show the apparatus 600 adapted to remove intact cells from localized zones 652 of the surgical site, in accordance with embodiments. In the exemplary embodiment of FIGS. 9A-9D, the apparatus is used to remove intact cells from a prostate P of a patient. The probe 450 of the apparatus may be threaded through the urethra U to reach the bladder B. As shown in FIGS. 9A and 9B, the probe may be retracted proximally in the direction indicated by arrow 201 to remove tissue from the base of the prostate P to the apex of the prostate such as with a liquid jet 620. As tissue is removed, the resected tissue may be suctioned through the ports 630 into a channel 632 that transport the tissue to filters.

In order to harvest tissue and cells from localized zones, the prostate P may be divided into cutting zones Z1, Z2, Z3, Z4, Z5, Z6, and Z7. The zones Z1, Z2, Z3, Z4, Z5, Z6, and Z7 may be sagittal zones and the probe (and the liquid jet) may be fully rotated as the probe is retracted. The zones Z1, Z2, Z3, Z4, Z5, Z6, and Z7 may be transverse zones and the probe (and the liquid jet) may be partially rotated as the probe is retracted.

As the liquid jet cuts in zone Z1, the resulting tissue fragments may be collected in a filter coupled to the ports, the filter being designated to receive tissue samples from zone Z1. As the liquid jet begins to move from cutting in zone Z1 to zone Z2, the apparatus may be configured to have a new filter receive the samples from zone Z2. Similarly, each time the liquid jet transitions from one cutting zone to the next, a new filter may be configured to replace the previous filter, so that tissue removed from each cutting zone is collected in a separate, appropriately designated filter.

The replacement of filters as the liquid jet transitions from one cutting zone to the next may be achieved in many ways. For example, each port may be located in a specific cutting zone, and coupled to a separate channel connected to a separate filter, each filter being designated for a specific cutting zone. Alternately, the channel coupling the ports to the filter may be further coupled to a plurality of channels connected to separate filters, and a valve may be disposed at the junction of these channels, such that the valve may be configured to redirect the removed tissue sample to a different filter as the liquid jet moves from one zone to the next.

The division of the prostate P into 7 cutting zones is for example only. Different numbers of divisions of the prostate P may be used. For example, a zone Z1 may be divided into two or more zones based on the depth of the tissue in relation to the probe (see zones Z1A, Z1B, and Z1C shown in FIG. 9C) and/or or based on radial location (see zones Z1X, Z1Y, and Z1Z shown in FIG. 9D).

Localized tissue and cell removal can help improve the diagnostic analysis of the removed samples and subsequent treatment of the resected organ. For example, in analyzing the removed tissue and cell samples for the detection of cancer, being able to analyze sample collected from distinct zones within the surgical site can provide information on where the cancerous tissue is located within the organ. By identifying the location of the cancer within the resected organ, therapy may be targeted rather than homogenous. Homogenous treatment may result in excess and unwanted collateral damage to neighboring tissues, vessels, nerve, as well as remaining non-cancerous tissue. The treatment may be adapted and dosed to reflect the severity of cancer between the different zones of the resected organ.

Localized tissue and cell removal can also help improve aspects of cell harvesting. For example, different areas within an organ can comprise different populations of cells, and being able to harvest cells from samples collected from distinct zones within an organ can help improve the efficiency of harvesting cells of a particular population. In the human prostate, prostate stem cells generally reside within the basal layer of the epithelial compartment at a low percentage of about 0.5-1% (Prajapati et al., Biomed Res Int 2013; 2013:107954). Localized tissue and cell removal can help to improve the efficiency of harvesting prostate stem cells for the generation of a pluripotent stem cell line, by enabling a more streamlined harvesting procedure wherein cells are harvested primarily from samples from local zones known to contain the stem cells.

Figure 11:
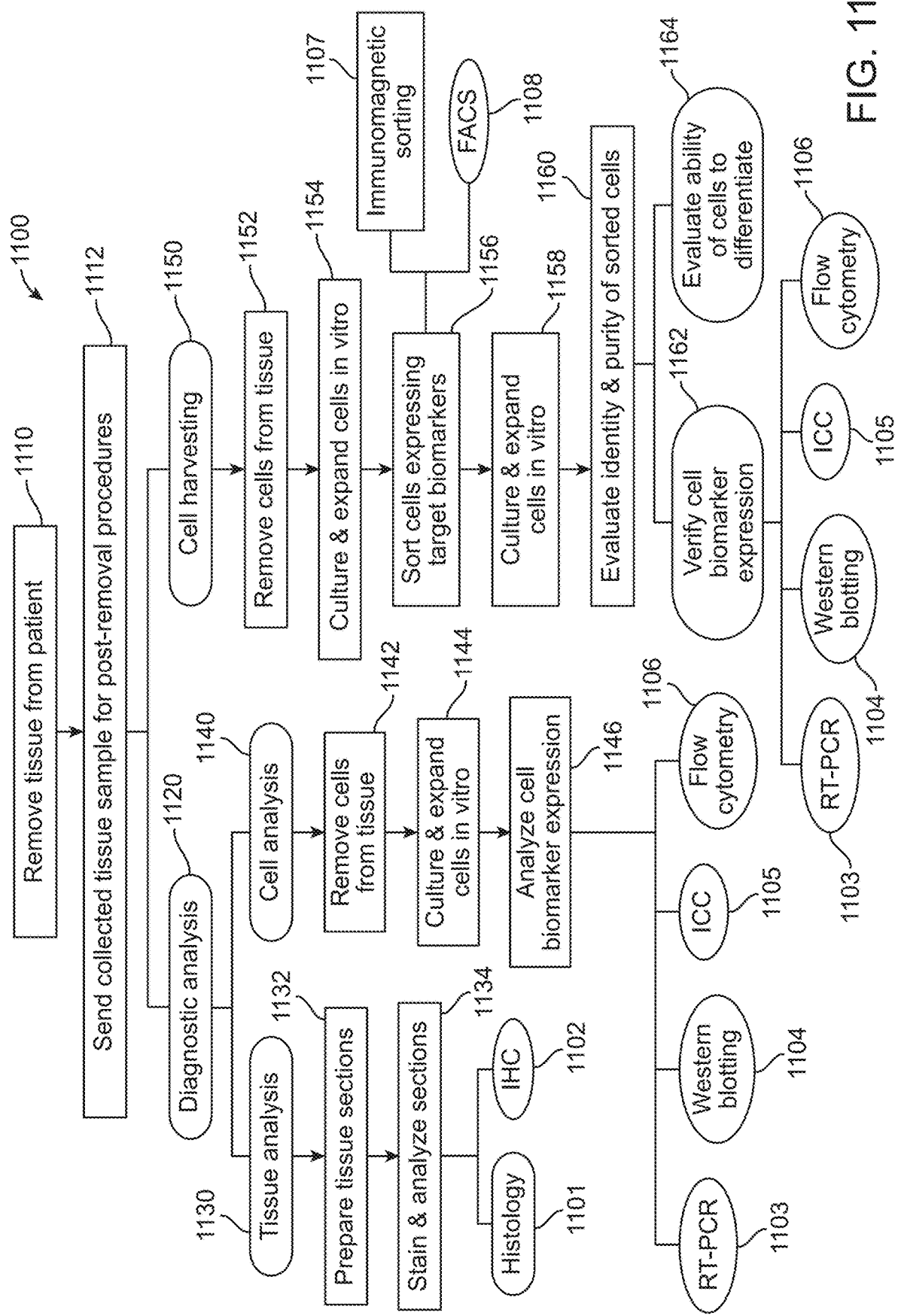
FIG. 11 shows a method of removing tissue comprising intact cells from a patient, in accordance with embodiments.

FIGS. 10A to 10D show images of histological sections of prostate tissue removed from patients using the apparatus 600 as described herein. The patients were human subjects treated for prostate hyperplasia as part of a clinical study. Each figure is a histological section from a different patient. Tissue fragments were removed from patients using an apparatus comprising a probe configured to deliver a liquid jet at the surgical site. The histological sections show that the apparatus is capable of removing large fragments of tissue with intact structural features, including intact cells 643, as shown by the dark-stained nuclei embedded throughout the tissue sections. Histological sections from 38 subjects have been taken, and all of these histological samples show intact stem cells. Based on the teachings provided herein a person of ordinary skill in the art can conduct testing to show that the nuclei of the cells of the tissue fragments comprise stem cells FIG. 11 shows a method 1100 of removing tissue comprising intact cells from a patient, in accordance with embodiments. At step 1110, tissue comprising intact cells is removed from the patient as described herein. At step 1112, one or more filters containing the one or more removed tissue samples are sent for post-removal procedures. Post-removal procedures may comprise, for example, the diagnostic analysis 1120 of the tissue samples or the harvesting of cells 1150 from the tissue samples.

The diagnostic analysis may comprise the analysis of tissue sections 1130 or the analysis of intact cells 1140. For tissue section analysis, at step 1132, tissue sections are prepared by fixing and slicing tissue fragment samples. At step 1134, the tissue sections are stained analyzed and analyzed, via a method such as histology 1101 or immunohistochemistry (IHC) 1102. For the analysis of intact cells, intact cells are first removed from the tissue samples at step 1142, for example via collagenase digestion of the tissue and centrifugation to separate cells from tissue. At step 1144, cells are cultured and expanded in vitro, and at step 1146, cells are analyzed for the expression of target biomarkers, via methods such as RT-PCR and gel electrophoresis 1103, western blotting 1104, immunocytochemistry (ICC) 1105, or flow cytometry 1106.

For the harvesting of cells from the tissue samples, cells are removed from the tissue at step 1152, for example via collagenase digestion of the tissue and centrifugation to separate cells from tissue. At step 1154, cells are cultured and expanded in vitro. At step 1156, cells expressing target biomarkers are sorted, via methods such as immunomagnetic sorting 1107 or fluorescence-activated cell sorting (FACS) 1108. At step 1158, sorted cells are further expanded in vitro. At step 1160, the identity and purity of the sorted and expanded cells is evaluated, by verifying the cells' expression of target biomarkers 1162 via methods such as RT-PCR and gel electrophoresis, western blotting, ICC, or flow cytometry, or by evaluating the ability of the cells to differentiate 1164 in vitro or in vivo.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method for removing intact cells from a surgical site of a patient, the method comprising:
   inserting a probe coupled to a nozzle into the surgical site;
   providing, by operating a pump at a first frequency and through the nozzle coupled to the probe, a continuous fluid stream through the nozzle that generates a plurality of shedding pulses comprising cavitations outside the nozzle, the plurality of shedding pulses outside the nozzle having a second frequency greater than the first frequency of the pump;
   resecting, with the plurality of shedding pulses comprising cavitations, tissue to create fragmented tissue comprising the intact cells;
   providing one or more filters to receive the fragmented tissue comprising the intact cells; and
   receiving, into the one or more filters, the fragmented tissue comprising the intact cells.

2. The method of claim 1, wherein the nozzle comprises an area of reduced diameter corresponding to a diameter of the continuous fluid stream released from the nozzle and wherein the nozzle is configured to dissociate the tissue into the fragmented tissue having dimensions sized larger than the reduced diameter.

3. The method of claim 1, wherein the nozzle and a port are arranged to provide a slurry to the port, the slurry comprising the fragmented tissue and fluid of the continuous fluid stream.

4. The method of claim 3, further comprising fragmenting the tissue with the cavitations of the shedding pulses.

5. The method of claim 4, further comprising immersing the nozzle in a liquid in order to generate the plurality of shedding pulses while the nozzle is immersed in the liquid.

6. The method of claim 1, further comprising providing a closed surgical site within the patient with the nozzle.

7. The method of claim 1, wherein the continuous fluid stream is generated by a first channel extending from a fluid source to the nozzle and a second channel extending from a port toward the one or more filters.

8. The method of claim 7, wherein the continuous fluid stream is generated by the pump connected to the first channel and providing a first flow rate of an injected fluid.

9. The method of claim 8, further comprising activating a second pump connected to the second channel to remove the fragmented tissue and the injected fluid at a second flow rate, wherein the first flow rate is similar to the second flow rate.

10. The method of claim 9, further comprising decreasing changes to a volume of a closed surgical site within the patient by providing a channel between a fluid reservoir and the surgical site in order to accommodate differences between the first flow rate and the second flow rate.

11. The method of claim 1, wherein the continuous fluid stream comprises one or more of a liquid or a gas.

12. The method of claim 1, wherein the continuous fluid stream comprises a liquid stream, the liquid stream comprising one or more of water or saline.

13. The method of claim 1, wherein resecting tissue comprises resecting tissue of a glandular tissue of an organ.

14. The method of claim 1, wherein a flow rate is within a range from 10 ml/min to 500 ml/min.

15. The method of claim 1, wherein an internal nozzle diameter is within a range from 50 um to 250 um.

16. The method of claim 1, further comprising rotating the nozzle around an elongate axis of the probe at a rate of from 10 degrees per second to 2000 degrees per second.

17. The method of claim 2, further comprising moving the nozzle along an elongate axis of the probe at a longitudinal velocity within a range from 0.01 mm/second to 50 mm/second.

18. The method of claim 2, wherein a time of a treatment with the continuous fluid stream is within a range from 0.1 minutes to 60 minutes.

19. The method of claim 1, further comprising rotating the probe about an elongate axis of the probe within a range from 0 to 360 degrees.

* * * * *